US012570997B2

(12) United States Patent
Gao et al.

(10) Patent No.: US 12,570,997 B2
(45) Date of Patent: Mar. 10, 2026

(54) FACTOR H VECTORS AND USES THEREOF

(71) Applicant: University of Massachusetts,
Westborough, MA (US)

(72) Inventors: Guangping Gao, Worcester, MA (US);
Jun Xie, Worcester, MA (US)

(73) Assignee: University of Massachusetts,
Westborough, MA (US)

( * ) Notice: Subject to any disclaimer, the term of this
patent is extended or adjusted under 35
U.S.C. 154(b) by 1148 days.

(21) Appl. No.: 17/602,343

(22) PCT Filed: Apr. 9, 2020

(86) PCT No.: PCT/US2020/027452
§ 371 (c)(1),
(2) Date: Oct. 8, 2021

(87) PCT Pub. No.: WO2020/210480
PCT Pub. Date: Oct. 15, 2020

(65) Prior Publication Data
US 2022/0162641 A1     May 26, 2022

Related U.S. Application Data

(60) Provisional application No. 62/831,870, filed on Apr.
10, 2019.

(51) Int. Cl.
*C12N 15/86*     (2006.01)
*C07K 14/47*     (2006.01)

(52) U.S. Cl.
CPC .......... *C12N 15/86* (2013.01); *C07K 14/4705*
(2013.01); *C07K 14/472* (2013.01); *C12N*
*2750/14143* (2013.01)

(58) Field of Classification Search
CPC .... C12N 2800/60; C12N 15/11; C12N 9/485;
C12N 2800/22; C12N 15/86; C12Y
304/14009; C07K 2317/23; C07K
2319/00; C07K 14/4702
USPC ...................................................... 435/69.1
See application file for complete search history.

(56) References Cited

U.S. PATENT DOCUMENTS

| | | | |
|---|---|---|---|
| 10,988,519 B2 * | 4/2021 | Song et al. | |
| 2018/0214576 A1 * | 8/2018 | Fitzgerald et al. | |
| 2018/0230488 A1 | 8/2018 | Hinderer et al. | |

FOREIGN PATENT DOCUMENTS

| | | |
|---|---|---|
| CN | 108291216 A | 7/2018 |
| JP | 2016-531910 A | 10/2016 |
| JP | 2018-527941 A | 9/2018 |
| WO | WO 2011/133890 A1 | 10/2011 |
| WO | WO 2015/023972 A1 | 2/2015 |
| WO | WO 2017/053732 A2 | 3/2017 |
| WO | WO 2018/106956 A2 | 6/2018 |

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*
PCT/US2020/027452, Jul. 7, 2020, Invitation to Pay Additional Fees.
PCT/US2020/027452, Sep. 30, 2020, International Search Report and Written Opinion.
PCT/US2020/027452, Oct. 21, 2021, International Preliminary Report on Patentability.
Lu et al., Advances in Transfer Methods For Gene Therapy. Foreign Medical Sciences (Section of Medgeography). Feb. 12, 1996. Issue 01. pp. 1-6.
Extended European Search Report for Application No. 20788329.9, mailed Nov. 21, 2022.
Borel et al., Recombinant AAV as a platform for translating the therapeutic potential of RNA interference. Mol Ther. Apr. 2014;22(4):692-701. doi: 10.1038/mt.2013.285. Epub Dec. 19, 2013.
Qiao et al., Liver-specific microRNA-122 target sequences incorporated in AAV vectors efficiently inhibits transgene expression in the liver. Gene Ther. Apr. 2011;18(4):403-10. doi: 10.1038/gt.2010. 157. Epub Dec. 9, 2010.
Xiao et al., Circumventing cellular immunity by miR142-mediated regulation sufficiently supports rAAV-delivered OVA expression without activating humoral immunity. JCI Insight. Jul. 11, 2019; 4(13): e99052. Published online Jul. 11, 2019. doi: 10.1172/jci. insight.99052.
Invitation to Pay Additional Fees for Application No. PCT/US2020/ 027452, mailed Jul. 7, 2020.
International Search Report and Written Opinion for Application No. PCT/US2020/027452, mailed Sep. 30, 2020.
International Preliminary Report on Patentability for Application No. PCT/US2020/027452, mailed Oct. 21, 2021.
Gu et al., Transduction of Adeno-Associated Virus Vectors Targeting Hair Cells and Supporting Cells in the Neonatal Mouse Cochlea. Front Cell Neurosci. Jan. 24, 2019:13:8. doi: 10.3389/fncel.2019. 00008. eCollection 2019.
EP 20788329.9, Nov. 21, 2022, Extended European Search Report.

* cited by examiner

*Primary Examiner* — Tekchand Saidha
*Assistant Examiner* — Mohammad Y Meah
(74) *Attorney, Agent, or Firm* — Wolf, Greenfield &
Sacks, P.C.

(57)     ABSTRACT

Aspects of the disclosure relate to compositions and methods for expressing a Factor H protein (or a variant thereof) in a cell or subject. In some embodiments, the disclosure provides isolated nucleic acids and rAAVs comprising a transgene encoding a Factor H protein variant and one or more regulatory sequences. In some embodiments, compositions described herein are useful for treating subjects having diseases associated with Factor H deficiency.

16 Claims, 4 Drawing Sheets

Specification includes a Sequence Listing.

SEQUENCE LISTING

<160> NUMBER OF SEQ ID NOS: 20

<210> SEQ ID NO 1
<211> LENGTH: 3695
<212> TYPE: DNA
<213> ORGANISM: Artificial Sequence
<220> FEATURE:
<223> OTHER INFORMATION: Synthetic Polynucleotide

<400> SEQUENCE: 1

```
atgagacttc tagcaaagat tatttgcctt atgttatggg ctatttgtgt agcagaagat      60
tgcaatgaac ttcctccaag aagaaataca gaaattctga caggttcctg gtctgaccaa     120
acatatccag aaggcaccca ggctatctat aaatgccgcc ctggatatag atctcttgga     180
aatataataa tggtatgcag gaagggagaa tgggttgctc ttaatccatt aaggaaatgt     240
cagaaaaggc cctgtggaca tcctggagat actcctttg gtacttttac ccttacagga     300
ggaaatgtgt ttgaatatgg tgtaaaagct gtgtatacat gtaatgaggg gtatcaattg     360
ctaggtgaga ttaattaccg tgaatgtgac acagatggat ggaccaatga tattcctata     420
tgtgaagttg tgaagtgttt accagtgaca gcaccagaga atggaaaaat tgtcagtagt     480
gcaatggaac cagatcggga ataccatttt ggacaagcag tacggtttgt atgtaactca     540
ggctacaaga ttgaaggaga tgaagaaatg cattgttcag acgatggttt ttggagtaaa     600
gagaaaccaa agtgtgtgga aatttcatgc aaatccccag atgttataaa tggatctcct     660
```

```
atatctcaga agattattta taaggagaat gaacgatttc aatataaatg taacatgggt        720
tatgaataca gtgaaagagg agatgctgta tgcactgaat ctggatggcg tccgttgcct        780
tcatgtgaag aaaaatcatg tgataatcct tatattccaa atggtgacta ctcaccttta        840
aggattaaac acagaactgg agatgaaatc acgtaccagt gtagaaatgg ttttttatcct        900 gcaacccggg gaaatacagc caaatgcaca agtactggct ggatacctgc tccgagatgt        960
accttgaaac cttgtgatta tccagacatt aaacatggag gtctatatca tgagaatatg       1020
cgtagaccat actttccagt agctgtagga aaatattact cctattactg tgatgaacat       1080
tttgagactc cgtcaggaag ttactgggat cacattcatt gcacacaaga tggatggtcg       1140
ccagcagtac catgcctcag aaaatgttat tttccttatt tggaaaatgg atataatcaa       1200
aattatggaa gaaagtttgt acagggtaaa tctatagacg ttgcctgcca tcctggctac       1260
gctcttccaa aagcgcagac cacagttaca tgtatggaga atggctggtc tcctactccc       1320
agatgcatcc gtgtcaaaac atgttccaaa tcaagtatag atattgagaa tgggtttatt       1380
tctgaatctc agtatacata tgccttaaaa gaaaaagcaa aatatcaatg caaactagga       1440
tatgtaacag cagatggtga aacatcagga tcaattacat gtgggaaaga tggatggtca       1500
gctcaaccca cgtgcattaa atcttgtgat atcccagtat ttatgaatgc cagaactaaa       1560
aatgacttca catggtttaa gctgaatgac acattggact atgaatgcca tgatggttat       1620
gaaagcaata ctggaagcac cactggttcc atagtgtgtg gttacaatgg ttggtctgat       1680
ttacccatat gttatgaaag agaatgcgaa cttcctaaaa tagatgtaca cttagttcct       1740
gatcgcaaga aagaccagta taaagttgga gaggtgttga aattctcctg caaaccagga       1800
tttacaatag ttggacctaa ttccgttcag tgctaccact ttggattgtc tcctgacctc       1860
ccaatatgta aagagcaagt acaatcatgt ggtccacctc ctgaactcct caatgggaat       1920
gttaaggaaa aaacgaaaga agaatatgga cacagtgaag tggtggaata ttattgcaat       1980
cctagatttc taatgaaggg acctaataaa attcaatgtg ttgatggaga gtggacaact       2040
ttaccagtgt gtattgtgga ggagagtacc tgtggagata tacctgaact tgaacatggc       2100
tgggcccagc tttcttcccc tccttattac tatggagatt cagtggaatt caattgctca       2160
gaatcattta caatgattgg acacagatca attacgtgta ttcatggagt atggacccaa       2220
cttccccagt gtgtggcaat agataaactt aagaagtgca aatcatcaaa tttaattata       2280
cttgaggaac atttaaaaaa caagaaggaa ttcgatcata attctaacat aaggtacaga       2340
tgtagaggaa aagaaggatg gatacacaca gtctgcataa atggaagatg ggatccagaa       2400
gtgaactgct caatggcaca aatacaatta tgcccacctc cacctcagat tcccaattct       2460
cacaatatga caaccacact gaattatcgg gatggagaaa aagtatctgt tctttgccaa       2520
gaaaattatc taattcagga aggagaagaa attacatgca aagatggaag atggcagtca       2580
ataccactct gtgttgaaaa aattccatgt tcacaaccac ctcagataga acacggaacc       2640
attaattcat ccaggtcttc acaagaaagt tatgcacatg gactaaatt gagttatact       2700 tgtgagggtg gtttcaggat atctgaagaa aatgaaacaa catgctacat gggaaaatgg       2760
agttctccac ctcagtgtga aggccttcct tgtaaatctc cacctgagat ttctcatggt       2820
gttgtagctc acatgtcaga cagttatcag tatggagaag aagttacgta caaatgtttt       2880
gaaggttttg gaattgatgg gcctgcaatt gcaaaatgct taggagaaaa atggtctcac       2940
cctccatcat gcataaaaac agattgtctc agtttaccta gctttgaaaa tgccataccc       3000
atgggagaga agaaggatgt gtataaggcg ggtgagcaag tgacttacac ttgtgcaaca       3060
```

-continued

```
tattacaaaa tggatggagc cagtaatgta acatgcatta atagcagatg gacaggaagg    3120
ccaacatgca gagacacctc ctgtgtgaat ccgcccacag tacaaaatgc ttatatagtg    3180
tcgagacaga tgagtaaata tccatctggt gagagagtac gttatcaatg taggagccct    3240
tatgaaatgt ttggggatga agaagtgatg tgtttaaatg gaaactggac ggaaccacct    3300
caatgcaaag attctacagg aaaatgtggg ccccctccac ctattgacaa tggggacatt    3360
acttcattcc cgttgtcagt atatgctcca gcttcatcag ttgagtacca atgccagaac    3420
ttgtatcaac ttgagggtaa caagcgaata acatgtagaa atggacaatg gtcagaacca    3480
ccaaaatgct tacatccgtg tgtaatatcc cgagaaatta tggaaaatta taacatagca    3540
ttaaggtgga cagccaaaca gaagctttat tcgagaacag gtgaatcagt tgaatttgtg    3600
tgtaaacggg gatatcgtct ttcatcacgt tctcacacat tgcgaacaac atgttgggat    3660
gggaaactgg agtatccaac ttgtgcaaaa agata    3695
```

```
<210> SEQ ID NO 2
<211> LENGTH: 1231
<212> TYPE: PRT
<213> ORGANISM: Artificial Sequence
<220> FEATURE:
<223> OTHER INFORMATION: Synthetic Polypeptide

<400> SEQUENCE: 2

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
```

```
                    245                     250                     255

Arg Pro Leu Pro Ser Cys Glu Glu Lys Ser Cys Asp Asn Pro Tyr Ile
            260                     265                     270

Pro Asn Gly Asp Tyr Ser Pro Leu Arg Ile Lys His Arg Thr Gly Asp
            275                     280                     285

Glu Ile Thr Tyr Gln Cys Arg Asn Gly Phe Tyr Pro Ala Thr Arg Gly
    290                     295                     300

Asn Thr Ala Lys Cys Thr Ser Thr Gly Trp Ile Pro Ala Pro Arg Cys
305                     310                     315                     320

Thr Leu Lys Pro Cys Asp Tyr Pro Asp Ile Lys His Gly Gly Leu Tyr
                325                     330                     335

His Glu Asn Met Arg Arg Pro Tyr Phe Pro Val Ala Val Gly Lys Tyr
            340                     345                     350

Tyr Ser Tyr Tyr Cys Asp Glu His Phe Glu Thr Pro Ser Gly Ser Tyr
            355                     360                     365

Trp Asp His Ile His Cys Thr Gln Asp Gly Trp Ser Pro Ala Val Pro
    370                     375                     380

Cys Leu Arg Lys Cys Tyr Phe Pro Tyr Leu Glu Asn Gly Tyr Asn Gln
385                     390                     395                     400

Asn Tyr Gly Arg Lys Phe Val Gln Gly Lys Ser Ile Asp Val Ala Cys
                405                     410                     415

His Pro Gly Tyr Ala Leu Pro Lys Ala Gln Thr Thr Val Thr Cys Met
            420                     425                     430

Glu Asn Gly Trp Ser Pro Thr Pro Arg Cys Ile Arg Val Lys Thr Cys
            435                     440                     445

Ser Lys Ser Ser Ile Asp Ile Glu Asn Gly Phe Ile Ser Glu Ser Gln
    450                     455                     460

Tyr Thr Tyr Ala Leu Lys Glu Lys Ala Lys Tyr Gln Cys Lys Leu Gly
465                     470                     475                     480

Tyr Val Thr Ala Asp Gly Glu Thr Ser Gly Ser Ile Thr Cys Gly Lys
                485                     490                     495

Asp Gly Trp Ser Ala Gln Pro Thr Cys Ile Lys Ser Cys Asp Ile Pro
            500                     505                     510

Val Phe Met Asn Ala Arg Thr Lys Asn Asp Phe Thr Trp Phe Lys Leu
            515                     520                     525

Asn Asp Thr Leu Asp Tyr Glu Cys His Asp Gly Tyr Glu Ser Asn Thr
    530                     535                     540

Gly Ser Thr Thr Gly Ser Ile Val Cys Gly Tyr Asn Gly Trp Ser Asp
545                     550                     555                     560

Leu Pro Ile Cys Tyr Glu Arg Glu Cys Glu Leu Pro Lys Ile Asp Val
                565                     570                     575

His Leu Val Pro Asp Arg Lys Lys Asp Gln Tyr Lys Val Gly Glu Val
            580                     585                     590

Leu Lys Phe Ser Cys Lys Pro Gly Phe Thr Ile Val Gly Pro Asn Ser
            595                     600                     605

Val Gln Cys Tyr His Phe Gly Leu Ser Pro Asp Leu Pro Ile Cys Lys
    610                     615                     620

Glu Gln Val Gln Ser Cys Gly Pro Pro Glu Leu Leu Asn Gly Asn
625                     630                     635                     640

Val Lys Glu Lys Thr Lys Glu Glu Tyr Gly His Ser Glu Val Val Glu
                645                     650                     655

Tyr Tyr Cys Asn Pro Arg Phe Leu Met Lys Gly Pro Asn Lys Ile Gln
            660                     665                     670
```

-continued

```
Cys Val Asp Gly Glu Trp Thr Thr Leu Pro Val Cys Ile Val Glu Glu
        675              680              685

Ser Thr Cys Gly Asp Ile Pro Glu Leu Glu His Gly Trp Ala Gln Leu
        690              695              700

Ser Ser Pro Pro Tyr Tyr Tyr Gly Asp Ser Val Glu Phe Asn Cys Ser
705              710              715              720

Glu Ser Phe Thr Met Ile Gly His Arg Ser Ile Thr Cys Ile His Gly
                725              730              735

Val Trp Thr Gln Leu Pro Gln Cys Val Ala Ile Asp Lys Leu Lys Lys
            740              745              750

Cys Lys Ser Ser Asn Leu Ile Ile Leu Glu Glu His Leu Lys Asn Lys
            755              760              765

Lys Glu Phe Asp His Asn Ser Asn Ile Arg Tyr Arg Cys Arg Gly Lys
        770              775              780

Glu Gly Trp Ile His Thr Val Cys Ile Asn Gly Arg Trp Asp Pro Glu
785              790              795              800

Val Asn Cys Ser Met Ala Gln Ile Gln Leu Cys Pro Pro Pro Gln
                805              810              815

Ile Pro Asn Ser His Asn Met Thr Thr Thr Leu Asn Tyr Arg Asp Gly
            820              825              830

Glu Lys Val Ser Val Leu Cys Gln Glu Asn Tyr Leu Ile Gln Glu Gly
            835              840              845

Glu Glu Ile Thr Cys Lys Asp Gly Arg Trp Gln Ser Ile Pro Leu Cys
        850              855              860

Val Glu Lys Ile Pro Cys Ser Gln Pro Pro Gln Ile Glu His Gly Thr
865              870              875              880

Ile Asn Ser Ser Arg Ser Ser Gln Glu Ser Tyr Ala His Gly Thr Lys
                885              890              895

Leu Ser Tyr Thr Cys Glu Gly Gly Phe Arg Ile Ser Glu Glu Asn Glu
            900              905              910

Thr Thr Cys Tyr Met Gly Lys Trp Ser Ser Pro Pro Gln Cys Glu Gly
            915              920              925

Leu Pro Cys Lys Ser Pro Pro Glu Ile Ser His Gly Val Val Ala His
        930              935              940

Met Ser Asp Ser Tyr Gln Tyr Gly Glu Glu Val Thr Tyr Lys Cys Phe
945              950              955              960

Glu Gly Phe Gly Ile Asp Gly Pro Ala Ile Ala Lys Cys Leu Gly Glu
                965              970              975

Lys Trp Ser His Pro Pro Ser Cys Ile Lys Thr Asp Cys Leu Ser Leu
            980              985              990

Pro Ser Phe Glu Asn Ala Ile Pro  Met Gly Glu Lys Lys  Asp Val Tyr
            995              1000             1005

Lys Ala  Gly Glu Gln Val Thr  Tyr Thr Cys Ala Thr  Tyr Tyr Lys
    1010             1015             1020

Met Asp  Gly Ala Ser Asn Val  Thr Cys Ile Asn Ser  Arg Trp Thr
    1025             1030             1035

Gly Arg  Pro Thr Cys Arg Asp  Thr Ser Cys Val Asn  Pro Pro Thr
    1040             1045             1050

Val Gln  Asn Ala Tyr Ile Val  Ser Arg Gln Met Ser  Lys Tyr Pro
    1055             1060             1065

Ser Gly  Glu Arg Val Arg Tyr  Gln Cys Arg Ser Pro  Tyr Glu Met
    1070             1075             1080
```

```
Phe Gly  Asp Glu Glu Val Met  Cys Leu Asn Gly Asn  Trp Thr Glu
    1085             1090              1095

Pro Pro  Gln Cys Lys Asp Ser  Thr Gly Lys Cys Gly  Pro Pro Pro
    1100             1105              1110

Pro Ile  Asp Asn Gly Asp Ile  Thr Ser Phe Pro Leu  Ser Val Tyr
    1115             1120              1125

Ala Pro  Ala Ser Ser Val Glu  Tyr Gln Cys Gln Asn  Leu Tyr Gln
    1130             1135              1140

Leu Glu  Gly Asn Lys Arg Ile  Thr Cys Arg Asn Gly  Gln Trp Ser
    1145             1150              1155

Glu Pro  Pro Lys Cys Leu His  Pro Cys Val Ile Ser  Arg Glu Ile
    1160             1165              1170

Met Glu  Asn Tyr Asn Ile Ala  Leu Arg Trp Thr Ala  Lys Gln Lys
    1175             1180              1185

Leu Tyr  Ser Arg Thr Gly Glu  Ser Val Glu Phe Val  Cys Lys Arg
    1190             1195              1200

Gly Tyr  Arg Leu Ser Ser Arg  Ser His Thr Leu Arg  Thr Thr Cys
    1205             1210              1215

Trp Asp  Gly Lys Leu Glu Tyr  Pro Thr Cys Ala Lys  Arg
    1220             1225              1230

<210> SEQ ID NO 3
<211> LENGTH: 701
<212> TYPE: PRT
<213> ORGANISM: Artificial Sequence
<220> FEATURE:
<223> OTHER INFORMATION: Synthetic Polypeptide

<400> SEQUENCE: 3

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205
```

-continued

```
Ser Cys Lys Ser Pro Asp Val Ile Asn Gly Ser Pro Ile Ser Gln Lys
    210             215                 220

Ile Ile Tyr Lys Glu Asn Glu Arg Phe Gln Tyr Lys Cys Asn Met Gly
225             230                 235                 240

Tyr Glu Tyr Ser Glu Arg Gly Asp Ala Val Cys Thr Glu Ser Gly Trp
            245                 250                 255

Arg Pro Leu Pro Ser Cys Glu Glu Lys Ser Thr Leu Lys Pro Cys Asp
            260                 265                 270

Tyr Pro Asp Ile Lys His Gly Gly Leu Tyr His Glu Asn Met Arg Arg
            275                 280                 285

Pro Tyr Phe Pro Val Ala Val Gly Lys Tyr Tyr Ser Tyr Tyr Cys Asp
    290                 295                 300

Glu His Phe Glu Thr Pro Ser Gly Ser Tyr Trp Asp His Ile His Cys
305                 310                 315                 320

Thr Gln Asp Gly Trp Ser Pro Ala Val Pro Cys Leu Arg Lys Cys Tyr
            325                 330                 335

Phe Pro Tyr Leu Glu Asn Gly Tyr Asn Gln Asn Tyr Gly Arg Lys Phe
            340                 345                 350

Val Gln Gly Lys Ser Ile Asp Val Ala Cys His Pro Gly Tyr Ala Leu
            355                 360                 365

Pro Lys Ala Gln Thr Thr Val Thr Cys Met Glu Asn Gly Trp Ser Pro
    370                 375                 380

Thr Pro Arg Cys Ile Arg Val Lys Thr Cys Ser Lys Ser Ser Ile Asp
385                 390                 395                 400

Ile Glu Asn Gly Phe Ile Ser Glu Ser Gln Tyr Thr Tyr Ala Leu Lys
            405                 410                 415

Glu Lys Ala Lys Tyr Gln Cys Lys Leu Gly Tyr Val Thr Ala Asp Gly
            420                 425                 430

Glu Thr Ser Gly Ser Ile Thr Cys Gly Lys Asp Gly Trp Ser Ala Gln
            435                 440                 445

Pro Thr Cys Ile Lys Ser Ile Lys Thr Asp Cys Leu Ser Leu Pro Ser
    450                 455                 460

Phe Glu Asn Ala Ile Pro Met Gly Glu Lys Lys Asp Val Tyr Lys Ala
465                 470                 475                 480

Gly Glu Gln Val Thr Tyr Thr Cys Ala Thr Tyr Tyr Lys Met Asp Gly
            485                 490                 495

Ala Ser Asn Val Thr Cys Ile Asn Ser Arg Trp Thr Gly Arg Pro Thr
            500                 505                 510

Cys Arg Asp Thr Ser Cys Val Asn Pro Pro Thr Val Gln Asn Ala Tyr
            515                 520                 525

Ile Val Ser Arg Gln Met Ser Lys Tyr Pro Ser Gly Glu Arg Val Arg
    530                 535                 540

Tyr Gln Cys Arg Ser Pro Tyr Glu Met Phe Gly Asp Glu Glu Val Met
545                 550                 555                 560

Cys Leu Asn Gly Asn Trp Thr Glu Pro Pro Gln Cys Lys Asp Ser Thr
            565                 570                 575

Gly Lys Cys Gly Pro Pro Pro Ile Asp Asn Gly Asp Ile Thr Ser
            580                 585                 590

Phe Pro Leu Ser Val Tyr Ala Pro Ala Ser Ser Val Glu Tyr Gln Cys
            595                 600                 605

Gln Asn Leu Tyr Gln Leu Glu Gly Asn Lys Arg Ile Thr Cys Arg Asn
    610                 615                 620

Gly Gln Trp Ser Glu Pro Pro Lys Cys Leu His Pro Cys Val Ile Ser
```

```
625              630              635              640

Arg Glu Ile Met Glu Asn Tyr Asn Ile Ala Leu Arg Trp Thr Ala Lys
                645              650              655

Gln Lys Leu Tyr Ser Arg Thr Gly Glu Ser Val Glu Phe Val Cys Lys
                660              665              670

Arg Gly Tyr Arg Leu Ser Ser Arg Ser His Thr Leu Arg Thr Thr Cys
                675              680              685

Trp Asp Gly Lys Leu Glu Tyr Pro Thr Cys Ala Lys Arg
        690              695              700

<210> SEQ ID NO 4
<211> LENGTH: 2106
<212> TYPE: DNA
<213> ORGANISM: Artificial Sequence
<220> FEATURE:
<223> OTHER INFORMATION: Synthetic Polynucleotide

<400> SEQUENCE: 4
atgagacttc tagcaaagat tatttgcctt atgttatggg ctatttgtgt agcagaagat        60
tgcaatgaac ttcctccaag aagaaataca gaaattctga caggttcctg gtctgaccaa       120
acatatccag aaggcacccca ggctatctat aaatgccgcc ctggatatag atctcttgga      180
aatataataa tggtatgcag gaagggagaa tgggttgctc ttaatccatt aaggaaatgt       240
cagaaaaggc cctgtggaca tcctggagat actccttttg gtacttttac ccttacagga       300
ggaaatgtgt ttgaatatgg tgtaaaagct gtgtatacat gtaatgaggg gtatcaattg       360
ctaggtgaga ttaattaccg tgaatgtgac acagatggat ggaccaatga tattcctata       420
tgtgaagttg tgaagtgttt accagtgaca gcaccagaga atggaaaaat tgtcagtagt       480
gcaatggaac cagatcggga ataccatttt ggacaagcag tacggtttgt atgtaactca       540
ggctacaaga ttgaaggaga tgaagaaatg cattgttcag acgatggttt ttggagtaaa       600
gagaaaccaa gtgtgtgga aatttcatgc aaatccccag atgttataaa tggatctcct        660
atatctcaga agattatttta taaggagaat gaacgatttc aatataaatg taacatgggt       720
tatgaataca gtgaaagagg agatgctgta tgcactgaat ctggatggcg tccgttgcct       780
tcatgtgaag aaaaatcaac cttgaaacct tgtgattatc cagacattaa acatggaggt       840
ctatatcatg agaatatgcg tagaccatac tttccagtag ctgtaggaaa atattactcc       900
tattactgtg atgaacattt tgagactccg tcaggaagtt actgggatca cattcattgc       960
acacaagatg gatggtcgcc agcagtacca tgcctcagaa aatgttattt tccttatttg      1020
gaaaatggat ataatcaaaa ttatggaaga aagtttgtac agggtaaatc tatagacgtt      1080
gcctgccatc ctggctacgc tcttccaaaa gcgcagacca cagttacatg tatggagaat      1140
ggctggtctc ctactcccag atgcatccgt gtcaaaacat gttccaaatc aagtatagat      1200
attgagaatg ggtttatttc tgaatctcag tatacatatg ccttaaaaga aaaagcaaaa      1260
tatcaatgca acctaggata tgtaacagca gatggtgaaa catcaggatc aattacatgt      1320
gggaaagatg gatggtcagc tcaacccacg tgcattaaat ctataaaaac agattgtctc      1380
agtttaccta gctttgaaaa tgccataccc atgggagaga agaaggatgt gtataaggcg      1440
ggtgagcaag tgacttacac ttgtgcaaca tattacaaaa tggatggagc cagtaatgta      1500
acatgcatta atagcagatg gacaggaagg ccaacatgca gagacacctc ctgtgtgaat      1560
ccgcccacag tacaaaatgc ttatatagtg tcgagacaga tgagtaaaata tccatctggt      1620 gagagagtac gttatcaatg taggagcccct tatgaaatgt ttgggatga agaagtgatg     1680
```

```
tgtttaaatg gaaactggac ggaaccacct caatgcaaag attctacagg aaaatgtggg      1740
ccccctccac ctattgacaa tggggacatt acttcattcc cgttgtcagt atatgctcca      1800
gcttcatcag ttgagtacca atgccagaac ttgtatcaac ttgagggtaa caagcgaata      1860
acatgtagaa atggacaatg gtcagaacca ccaaaatgct tacatccgtg tgtaatatcc      1920
cgagaaatta tggaaaatta taacatagca ttaaggtgga cagccaaaca gaagctttat      1980
tcgagaacag gtgaatcagt tgaatttgtg tgtaaacggg gatatcgtct ttcatcacgt      2040
tctcacacat tgcgaacaac atgttgggat gggaaactgg agtatccaac ttgtgcaaaa      2100
agatag                                                                 2106
```

```
<210> SEQ ID NO 5
<211> LENGTH: 4549
<212> TYPE: DNA
<213> ORGANISM: Artificial Sequence
<220> FEATURE:
<223> OTHER INFORMATION: Synthetic Polynucleotide

<400> SEQUENCE: 5
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact       120
aggggttcct tgtagttaat gattaacccg ccatgctact tatctaccag ggtaatgggg       180
atcctctaga actatagcta gtcgacattg attattgact agttattaat agtaatcaat       240
tacggggtca ttagttcata gcccatatat ggagttccgc gttacataac ttacggtaaa       300
tggcccgcct ggctgaccgc ccaacgaccc ccgcccattg acgtcaataa tgacgtatgt       360
tcccatagta acgccaatag ggactttcca ttgacgtcaa tgggtggagt atttacggta       420
aactgcccac ttggcagtac atcaagtgta tcatatgcca agtacgcccc ctattgacgt       480
caatgacggt aaatggcccg cctggcatta tgcccagtac atgaccttat gggactttcc       540
tacttggcag tacatctacg tattagtcat cgctattacc atggtcgagg tgagccccac       600
gttctgcttc actctcccca tctcccccccc ctccccaccc caattttgt atttatttat       660 tttttaatta ttttgtgcag cgatgggggc ggggggggg gggggcgcg cgccaggcgg       720 ggcggggcgg ggcgagggc ggggcggggc gaggcggaga ggtgcggcgg cagccaatca       780
gagcggcgcg ctccgaaagt ttccttttat ggcgaggcgg cggcggcggc ggccctataa       840
aaagcgaagc gcgcggcggg cggggagtcg ctgcgacgct gccttcgccc cgtgccccgc       900
tccgccgccg cctcgcgccg cccgccccgg ctctgactga ccgcgttact cccacaggtg       960
agcgggcggg acggccctc tcctccgggc tgtaattagc gcttggttta atgacggctt      1020
gtttcttttc tgtggctgcg tgaaagcctt gaggggctcc gggagggccc tttgtgcggg      1080
gggagcggct cgggggtgc gtgcgtgtgt gtgtgcgtgg ggagcgccgc gtgcggctcc      1140
gcgctgcccg gcggctgtga gcgctgcggg cgcggcgcgg ggctttgtgc gctccgcagt      1200
gtgcgcgagg ggagcgcggc cggggggcggt gccccgcggt gcgggggggg ctgcgagggg      1260
aacaaaggct gcgtgcgggg tgtgtgcgtg gggggggtgag caggggggtgt gggcgcgtcg      1320 gtcgggctgc aacccccct gcacccccct ccccgagttg ctgagcacgg cccggcttcg      1380
ggtgcggggc tccgtacggg gcgtggcgcg gggctcgccg tgccgggcgg ggggtggcgg      1440
caggtggggg tgccgggcgg ggcggggccg cctcgggccg gggagggctc ggggggagggg      1500 cgcggcggcc cccggagcgc cggcggctgt cgaggcgcgc cgagccgcag ccattgcctt      1560
```

-continued

```
ttatggtaat cgtgcgagag ggcgcaggga cttcctttgt cccaaatctg tgcggagccg    1620
aaatctggga ggcgccgccg cacccctct agcgggcgcg gggcgaagcg gtgcggcgcc    1680
ggcaggaagg aaatgggcgg ggagggcctt cgtgcgtcgc cgcgccgccg tcccttctc    1740 cctctccagc ctcggggctg tccgcggggg gacggctgcc ttcggggggg acggggcagg    1800
gcggggttcg gcttctggcg tgtgaccggc ggctctagag cctctgctaa ccatgttcat    1860
gccttcttct ttttcctaca gctcctgggc aacgtgctgg ttattgtgct gtctcatcat    1920
tttggcaaag aattcgccac catgcgcctg ctggccaaga tcatctgcct gatgctgtgg    1980
gccatctgcg tggccgagga ctgtaacgag ctgcccctc ggagaaatac agagatcctg    2040
accggctctt ggagcgatca gacctaccca gagggcacac aggccatcta caagtgcagg    2100
cccggctatc gctccctggg caatatcatc atggtgtgca ggaagggaga gtgggtggcc    2160
ctgaacccac tgagaaagtg ccagaagagg ccatgtggac acccaggcga cacacctttc    2220
ggcaccttta cactgaccgg cggcaacgtg ttcgagtacg gcgtgaaggc cgtgtatacc    2280
tgcaatgagg gctaccagct gctgggcgag atcaactacc gggagtgtga cacagatggc    2340
tggaccaatg atatccccat ctgcgaggtg gtgaagtgtc tgccagtgac cgcccccgag    2400
aacggcaaga tcgtgagctc cgccatggag cctgacagag agtatcactt cggccaggcc    2460
gtgaggttcg tgtgcaatag cggctacaag atcgagggcg atgaggagat gcactgttcc    2520
gacgatggct tctggtctaa ggagaagccc aagtgcgtgg agatctcctg taagtctcct    2580
gacgtgatta acggcagccc aatctcccag aagatcatct ataaggagaa tgagcggttt    2640
cagtacaagt gcaacatggg ctacgagtat tccgagagag cgatgccgt gtgcacagag    2700 tctggatgga ggcccctgcc tagctgcgag gagaagtcca ccctgaagcc ttgtgactat    2760
ccagatatca agcacggcgg cctgtatcac gagaatatga ggcgcccta cttcccagtg    2820 gccgtgggca agtactattc ctactattgc gacgagcact ttgagacacc atccggctct    2880
tactgggacc acatccactg tacccaggat ggctggtctc ccgccgtgcc ttgcctgaga    2940
aagtgttact ccctatct ggagaacggc tacaaccaga attatggcag gaagtttgtg    3000
cagggcaagt ccatcgacgt ggcatgccac ccaggatacg cactgcctaa ggcacagacc    3060
acagtgacct gtatggagaa tggctggagc ccaacacca ggtgcatccg cgtgaagacc    3120
tgttccaaga gcagcatcga catcgagaac ggcttcatca gcgagtccca gtacaccctat    3180 gccctgaagg agaaggccaa gtatcagtgc aagctgggat acgtgaccgc agacggagag    3240
acatctggca gcatcacctg cggcaaggat ggctggtctg cccagcccac atgcatcaag    3300
agcatcaaga ccgactgtct gtctctgccc agctttgaga tgccatccc tatgggcgag    3360 aagaaggacg tgtacaaggc cggcgagcag gtgacataca cctgcgccac atactataag    3420
atggacggcg ccagcaacgt gacctgtatc aattcccggt ggacaggcag acctacctgc    3480
agggatacaa gctgcgtgaa cccacccacc gtgcagaatg cctatatcgt gtcccgccag    3540
atgtctaagt accctagcgg cgagcgggtg agatatcagt gccggtcccc atacgagatg    3600
ttcggcgacg aggaagtgat gtgcctgaac ggcaattgga cagagcctcc acagtgcaag    3660
gatagcaccg gcaagtgtgg accacctcca ccaatcgaca acggcgatat cacatccttt    3720
ccactgagcg tgtacgcccc cgcctcctct gtggagtatc agtgccagaa cctgtaccag    3780
ctggagggca ataagcgcat cacctgtcgg aacggccagt ggtctgagcc tccaaagtgc    3840
ctgcaccctt gcgtgatctc cagagagatc atggagaact ataatatcgc cctgcgctgg    3900
acagccaagc agaagctgta ctctcggacc ggcgagagcg tggagttcgt gtgcaagcgg    3960
```

```
ggctatagac tgagctcccg cagccacaca ctgcggacca catgctggga cggcaagctg    4020
gagtacccaa cctgtgccaa gaggtgagcg gccgctccat aaagtaggaa acactacatc    4080
cataaagtag gaaacactac atccataaag taggaaacac tacagcggcc gcgtcgacac    4140
gcgtggtacc tctagagtcg acccgggcgg cctcgaggac ggggtgaact acgcctgagg    4200
atccgatctt tttccctctg ccaaaaatta tggggacatc atgaagcccc ttgagcatct    4260
gacttctggc taataaagga aatttatttt cattgcaata gtgtgttgga attttttgtg    4320
tctctcactc ggaagcaatt cgttgatctg aatttcgacc acccataata cccattaccc    4380
tggtagataa gtagcatggc gggttaatca ttaactacaa ggaacccctag tgatggagt    4440 tggccactcc ctctctgcgc gctcgctcgc tcactgaggc cgggcgacca aaggtcgccc    4500
gacgcccggg ctttgcccgg gcggcctcag tgagcgagcg agcgcgcag              4549
```

```
<210> SEQ ID NO 6
<211> LENGTH: 4472
<212> TYPE: DNA
<213> ORGANISM: Artificial Sequence
<220> FEATURE:
<223> OTHER INFORMATION: Synthetic Polynucleotide

<400> SEQUENCE: 6
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggagt atttacggta     420
aactgcccac ttggcagtac atcaagtgta tcatatgcca gtacgcccc ctattgacgt      480 caatgacggt aaatggcccg cctggcatta tgcccagtac atgaccttat gggactttcc     540
tacttggcag tacatctacg tattagtcat cgctattacc atggtcgagg tgagccccac     600
gttctgcttc actctcccca tctcccccc ctccccaccc caattttgt atttatttat        660 tttttaatta ttttgtgcag cgatggggc gggggggggg gggggcgcg cgccaggcgg        720 ggcggggcgg ggcgagggc ggggcggggc gaggcggaga ggtgcggcgg cagccaatca      780
gagcggcgcg ctccgaaagt ttcctttat ggcgaggcgg cggcggcggc ggccctataa       840
aaagcgaagc gcgcggcggg cggggagtcg ctgcgacgct gccttcgccc cgtgccccgc      900
tccgccgccg cctcgcgccg cccgcccgg ctctgactga ccgcgttact cccacaggtg       960
agcgggcggg acggcccttc tcctccgggc tgtaattagc gcttggttta atgacggctt     1020
gtttcttttc tgtggctgcg tgaaagcctt gaggggctcc gggagggccc tttgtgcggg     1080
gggagcggct cggggggtgc gtgcgtgtgt gtgtgcgtgg ggagcgccgc gtgcggctcc     1140
gcgctgcccg gcggctgtga gcgctgcggg cgcggcgcgg ggctttgtgc gctccgcagt     1200
gtgcgcgagg ggagcgcggc cgggggcggt gccccgcggt gcggggggg ctgcgagggg      1260 aacaaaggct gcgtgcgggg tgtgtgcgtg gggggtgag caggggggtgt gggcgcgtcg     1320 gtcgggctgc aacccccct gcacccccct ccccgagttg ctgagcacgg cccggcttcg      1380
ggtgcggggc tccgtacggg gcgtggcgcg gggctcgccg tgccgggcgg ggggtggcgg     1440
```

-continued

```
caggtggggg tgccgggcgg ggcggggccg cctcgggccg gggagggctc gggggagggg    1500
cgcggcggcc cccggagcgc cggcggctgt cgaggcgcgg cgagccgcag ccattgcctt    1560
ttatggtaat cgtgcgagag ggcgcaggga cttcctttgt cccaaatctg tgcggagccg    1620
aaatctggga ggcgccgccg caccccctct agcgggcgcg gggcgaagcg gtgcggcgcc    1680
ggcaggaagg aaatgggcgg ggagggcctt cgtgcgtcgc cgcgccgccg tccccttctc    1740
cctctccagc ctcggggctg tccgcggggg gacggctgcc ttcggggggg acggggcagg    1800
gcggggttcg gcttctggcg tgtgaccggc ggctctagag cctctgctaa ccatgttcat    1860
gccttcttct ttttcctaca gctcctgggc aacgtgctgg ttattgtgct gtctcatcat    1920
tttggcaaag aattcgccac catgcgcctg ctggccaaga tcatctgcct gatgctgtgg    1980
gccatctgcg tggccgagga ctgtaacgag ctgccccctc ggagaaatac agagatcctg    2040
accggctctt ggagcgatca gacctaccca gagggcacac aggccatcta caagtgcagg    2100
cccggctatc gctccctggg caatatcatc atggtgtgca ggaagggaga gtgggtggcc    2160
ctgaacccac tgagaaagtg ccagaagagg ccatgtggac acccaggcga cacacctttc    2220 ggcacctttta cactgaccgg cggcaacgtg ttcgagtacg gcgtgaaggc cgtgtatacc    2280
tgcaatgagg gctaccagct gctgggcgag atcaactacc gggagtgtga cacagatggc    2340
tggaccaatg atatccccat ctgcgaggtg gtgaagtgtc tgccagtgac cgcccccgag    2400
aacggcaaga tcgtgagctc cgccatggag cctgacagag agtatcactt cggccaggcc    2460
gtgaggttcg tgtgcaatag cggctacaag atcgagggcg atgaggagat gcactgttcc    2520
gacgatggct tctggtctaa ggagaagccc aagtgcgtgg agatctcctg taagtctcct    2580
gacgtgatta acggcagccc aatctcccag aagatcatct ataaggagaa tgagcggttt    2640
cagtacaagt gcaacatggg ctacgagtat tccgagagag gcgatgccgt gtgcacagag    2700
tctggatgga ggcccctgcc tagctgcgag gagaagtcca ccctgaagcc ttgtgactat    2760
ccagatatca gcacggcggg cctgtatcac gagaatatga ggcgccctta cttcccagtg    2820
gccgtgggca gtactattc ctactattgc gacgagcact ttgagacacc atccggctct    2880
tactgggacc acatccactg tacccaggat ggctggtctc ccgccgtgcc ttgcctgaga    2940
aagtgttact tccctatct ggagaacggc tacaaccaga attatggcag gaagtttgtg    3000
cagggcaagt ccatcgacgt ggcatgccac ccaggatacg cactgcctaa ggcacagacc    3060
acagtgacct gtatggagaa tggctggagc ccaacaccca ggtgcatccg cgtgaagacc    3120
tgttccaaga gcagcatcga catcgagaac ggcttcatca gcgagtccca gtacacctat    3180
gccctgaagg agaaggccaa gtatcagtgc aagctgggat acgtgaccgc agacggagag    3240
acatctggca gcatcacctg cggcaaggat ggctggtctg cccagcccac atgcatcaag    3300
agcatcaaga ccgactgtct gtctctgccc agctttgaga tgccatccc tatgggcgag    3360 aagaaggacg tgtacaaggc cggcgagcag gtgacataca cctgcgccac atactataag    3420
atggacggcg ccagcaacgt gacctgtatc aattcccggt ggacaggcag acctacctgc    3480
agggatacaa gctgcgtgaa cccacccacc gtgcagaatg cctatatcgt gtcccgccag    3540
atgtctaagt accctagcgg cgagcgggtg agatatcagt gccggtcccc atacgagatg    3600
ttcggcgacg aggaagtgat gtgcctgaac ggcaattgga cagagcctcc acagtgcaag    3660
gatagcaccg gcaagtgtgg accacctcca ccaatcgaca acggcgatat cacatccttt    3720
ccactgagcg tgtacgcccc cgcctcctct gtggagtatc agtgccagaa cctgtaccag    3780
ctggagggca ataagcgcat cacctgtcgg aacggccagt ggtctgagcc tccaaagtgc    3840
```

-continued

```
ctgcaccctt gcgtgatctc cagagagatc atggagaact ataatatcgc cctgcgctgg    3900
acagccaagc agaagctgta ctctcggacc ggcgagagcg tggagttcgt gtgcaagcgg    3960
ggctatagac tgagctcccg cagccacaca ctgcggacca catgctggga cggcaagctg    4020
gagtacccaa cctgtgccaa gaggtgagcg gccgcgtcga cacgcgtggt acctctagag    4080
tcgacccggg cggcctcgag gacggggtga actacgcctg aggatccgat cttttttccct    4140 ctgccaaaaa ttatggggac atcatgaagc cccttgagca tctgacttct ggctaataaa    4200
ggaaatttat tttcattgca atagtgtgtt ggaattttttt gtgtctctca ctcggaagca    4260
attcgttgat ctgaatttcg accacccata atacccatta ccctggtaga taagtagcat    4320
ggcgggttaa tcattaacta caaggaaccc ctagtgatgg agttggccac tccctctctg    4380
cgcgctcgct cgctcactga ggccgggcga ccaaaggtcg cccgacgccc gggctttgcc    4440
cgggcggcct cagtgagcga gcgagcgcgc ag    4472
```

<210> SEQ ID NO 7
<211> LENGTH: 3525
<212> TYPE: DNA
<213> ORGANISM: Artificial Sequence
<220> FEATURE:
<223> OTHER INFORMATION: Synthetic Polynucleotide

<400> SEQUENCE: 7

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctacgcg tcgacattga ttattgactc tggtcgttac    180
ataacttacg gtaaatggcc cgcctggctg accgcccaac gacccgccc attgacgtca    240 ataatgacgt atgttcccat agtaacgcca atagggactt tccattgacg tcaatgggtg    300
gagtatttac ggtaaactgc ccacttggca gtacatcaag tgtatcatat gccaagtacg    360 cccctattg acgtcaatga cggtaaatgg cccgcctggc attatgccca gtacatgacc    420
ttatgggact ttcctacttg gcagtacatc tactcgaggc cacgttctgc ttcactctcc    480
ccatctcccc ccctcccca cccccaattt tgtatttatt tattttttaa ttattttgtg    540
cagcgatggg ggcggggggg ggggggggg gggcgcgcgc caggcggggc ggggcggggc    600
gaggggcggg gcggggcgag gcggagaggt gcggcggcag ccaatcagag cggcgcgctc    660
cgaaagtttc cttttatggc gaggcggcgg cggcggcggc cctataaaaa gcgaagcgcg    720
cggcgggcgg gagcgggatc agccaccgcg gtggcggccc tagagtcgat cgaggaactg    780
aaaaaccaga aagttaactg gtaagtttag tcttttttgtc ttttatttca ggtcccggat    840
ccggtggtgg tgcaaatcaa agaactgctc ctcagtggat gttgccttta cttctaggcc    900
tgtacggaag tgttacttct gctctaaaag ctgcggaatt gtacccgcgg ccgatccacc    960
ggtatcgatg ccaccatgag acttctagca aagattattt gccttatgtt atgggctatt   1020
tgtgtagcag aagattgcaa tgaacttcct ccaagaagaa atacagaaat ctgacaggt   1080 tcctggtctg accaaacata tccagaaggc acccaggcta tctataaatg ccgccctgga   1140
tatagatctc ttggaaatat aataatggta tgcaggaagg gagaatgggt tgctcttaat   1200
ccattaagga aatgtcagaa aaggccctgt ggacatcctg gagatactcc ttttggtact   1260
tttaccctta caggaggaaa tgtgtttgaa tatggtgtaa aagctgtgta tacatgtaat   1320
gaggggtatc aattgctagg tgagattaat taccgtgaat gtgacacaga tggatggacc   1380
```

-continued

```
aatgatattc ctatatgtga agttgtgaag tgtttaccag tgacagcacc agagaatgga    1440
aaaattgtca gtagtgcaat ggaaccagat cgggaatacc attttggaca agcagtacgg    1500
tttgtatgta actcaggcta caagattgaa ggagatgaag aaatgcattg ttcagacgat    1560
ggtttttgga gtaaagagaa accaaagtgt gtggaaattt catgcaaatc cccagatgtt    1620
ataaatggat ctcctatatc tcagaagatt atttataagg agaatgaacg atttcaatat    1680
aaatgtaaca tgggttatga atacagtgaa agaggagatg ctgtatgcac tgaatctgga    1740
tggcgtccgt tgccttcatg tgaagaaaaa tcaaccttga aaccttgtga ttatccagac    1800
attaaacatg gaggtctata tcatgagaat atgcgtagac catactttcc agtagctgta    1860
ggaaaatatt actcctatta ctgtgatgaa cattttgaga ctccgtcagg aagttactgg    1920
gatcacattc attgcacaca agatggatgg tcgccagcag taccatgcct cagaaaatgt    1980
tattttcctt atttggaaaa tggatataat caaaattatg gaagaaagtt tgtacagggt    2040
aaatctatag acgttgcctg ccatcctggc tacgctcttc caaaagcgca gaccacagtt    2100
acatgtatgg agaatggctg gtctcctact cccagatgca tccgtgtcaa aacatgttcc    2160
aaatcaagta tagatattga gaatgggttt atttctgaat ctcagtatac atatgcctta    2220
aaagaaaaag caaaatatca atgcaaacta ggatatgtaa cagcagatgg tgaaacatca    2280
ggatcaatta catgtgggaa agatggatgg tcagctcaac ccacgtgcat taaatctata    2340
aaaacagatt gtctcagttt acctagcttt gaaaatgcca tacccatggg agagaagaag    2400
gatgtgtata aggcgggtga gcaagtgact tacacttgtg caacatatta caaaatggat    2460
ggagccagta atgtaacatg cattaatagc agatggacag gaaggccaac atgcagagac    2520
acctcctgtg tgaatccgcc cacagtacaa aatgcttata tagtgtcgag acagatgagt    2580
aaatatccat ctggtgagag agtacgttat caatgtagga gcccttatga aatgtttggg    2640
gatgaagaag tgatgtgttt aaatggaaac tggacggaac cacctcaatg caaagattct    2700
acaggaaaat gtgggccccc tccacctatt gacaatgggg acattacttc attcccgttg    2760
tcagtatatg ctccagcttc atcagttgag taccaatgcc agaacttgta tcaacttgag    2820
ggtaacaagc gaataacatg tagaaatgga caatggtcag aaccaccaaa atgcttacat    2880
ccgtgtgtaa tatcccgaga aattatggaa aattataaca tagcattaag gtggacagcc    2940
aaacagaagc tttattcgag aacaggtgaa tcagttgaat ttgtgtgtaa acggggatat    3000
cgtctttcat cacgttctca cacattgcga acaacatgtt gggatgggaa actggagtat    3060
ccaacttgtg caaaaagata ggcggccgct ccataaagta ggaaacacta catccataaa    3120
gtaggaaaca ctacatccat aaagtaggaa acactacagc ggccgcgtcg actgatcagc    3180
ctcgactgtg ccttctagtt gccagccatc tgttgtttgc ccctcccccg tgccttcctt    3240
gaccctggaa ggtgccactc ccactgtcct ttcctaataa aatgaggaaa ttgcatcgca    3300
ttgtctgagt aggtgtcatt ctattctggg gggtggggtg gggcaggaca gcaaggggga    3360
ggattgggaa gacaagatct aggaacccct agtgatggag ttggccactc cctctctgcg    3420
cgctcgctcg ctcactgagg ccgcccgggc aaagcccggg cgtcgggcga cctttggtcg    3480
cccggcctca gtgagcgagc gagcgcgcag agagggagtg gccaa    3525
```

<210> SEQ ID NO 8
<211> LENGTH: 3448
<212> TYPE: DNA
<213> ORGANISM: Artificial Sequence
<220> FEATURE:
<223> OTHER INFORMATION: Synthetic Polynucleotide -continued

```
<400> SEQUENCE: 8
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctacgcg tcgacattga ttattgactc tggtcgttac     180
ataacttacg gtaaatggcc cgcctggctg accgcccaac gacccgccc  attgacgtca     240 ataatgacgt atgttcccat agtaacgcca atagggactt tccattgacg tcaatgggtg     300
gagtatttac ggtaaactgc ccacttggca gtacatcaag tgtatcatat gccaagtacg     360
ccccctattg acgtcaatga cggtaaatgg cccgcctggc attatgccca gtacatgacc     420
ttatgggact ttcctacttg gcagtacatc tactcgaggc cacgttctgc ttcactctcc     480
ccatctcccc cccctcccca ccccaattt  tgtatttatt tattttttaa ttattttgtg     540
cagcgatggg ggcgggggg  ggggggggg  gggcgcgcgc caggcggggc ggggcggggc     600
gaggggcggg gcgggcgag  gcggagaggt gcggcggcag ccaatcagag cggcgcgctc     660
cgaaagtttc cttttatggc gaggcggcgg cggcggcggc cctataaaaa gcgaagcgcg     720
cggcgggcgg gagcgggatc agccaccgcg gtggcggccc tagagtcgat cgaggaactg     780
aaaaaccaga aagttaactg gtaagtttag tcttttttgtc ttttatttca ggtcccggat     840 ccggtggtg  tgcaaatcaa agaactgctc ctcagtggat gttgccttta cttctaggcc     900
tgtacggaag tgttacttct gctctaaaag ctgcggaatt gtacccgcgg ccgatccacc     960
ggtatcgatg ccaccatgag acttctagca aagattattt gccttatgtt atgggctatt    1020
tgtgtagcag aagattgcaa tgaacttcct ccaagaagaa atacagaaat tctgacaggt    1080
tcctggtctg accaaacata tccagaaggc acccaggcta tctataaatg ccgccctgga    1140
tatagatctc ttggaaatat aataatggta tgcaggaagg gagaatgggt tgctcttaat    1200
ccattaagga aatgtcagaa aaggccctgt ggacatcctg gagatactcc ttttggtact    1260 tttacccttta caggaggaaa tgtgtttgaa tatggtgtaa aagctgtgta tacatgtaat    1320
gaggggtatc aattgctagg tgagattaat taccgtgaat gtgacacaga tggatggacc    1380
aatgatattc ctatatgtga agttgtgaag tgtttaccag tgacagcacc agagaatgga    1440
aaaattgtca gtagtgcaat ggaaccagat cgggaatacc atttttggaca agcagtacgg    1500 tttgtatgta actcaggcta caagattgaa ggagatgaag aaatgcattg ttcagacgat    1560 ggttttttgga gtaaagagaa accaaagtgt gtggaaattt catgcaaatc cccagatgtt    1620
ataaatggat ctcctatatc tcagaagatt atttataagg agaatgaacg atttcaatat    1680
aaatgtaaca tgggttatga atacagtgaa agaggagatg ctgtatgcac tgaatctgga    1740
tggcgtccgt tgccttcatg tgaagaaaaa tcaaccttga aaccttgtga ttatccagac    1800
attaaacatg gaggtctata tcatgagaat atgcgtagac catactttcc agtagctgta    1860
ggaaaatatt actcctatta ctgtgatgaa cattttgaga ctccgtcagg aagttactgg    1920
gatcacattc attgcacaca agatggatgg tcgccagcag taccatgcct cagaaaatgt    1980
tattttcctt atttggaaaa tggatataat caaaattatg gaagaaagtt tgtacagggt    2040
aaatctatag acgttgcctg ccatcctggc tacgctcttc caaaagcgca gaccacagtt    2100
acatgtatgg agaatggctg gtctcctact cccagatgca tccgtgtcaa aacatgttcc    2160
aaatcaagta tagatattga gaatgggttt atttctgaat ctcagtatac atatgcctta    2220
aaagaaaaag caaaatatca atgcaaacta ggatatgtaa cagcagatgg tgaaacatca    2280
```

-continued

```
ggatcaatta catgtgggaa agatggatgg tcagctcaac ccacgtgcat taaatctata    2340
aaaacagatt gtctcagttt acctagcttt gaaaatgcca tacccatggg agagaagaag    2400
gatgtgtata aggcgggtga gcaagtgact tacacttgtg caacatatta caaaatggat    2460
ggagccagta atgtaacatg cattaatagc agatggacag gaaggccaac atgcagagac    2520
acctcctgtg tgaatccgcc cacagtacaa aatgcttata tagtgtcgag acagatgagt    2580
aaatatccat ctggtgagag agtacgttat caatgtagga gcccttatga aatgtttggg    2640
gatgaagaag tgatgtgttt aaatggaaac tggacggaac cacctcaatg caaagattct    2700
acaggaaaat gtgggccccc tccacctatt gacaatgggg acattacttc attcccgttg    2760
tcagtatatg ctccagcttc atcagttgag taccaatgcc agaacttgta tcaacttgag    2820
ggtaacaagc gaataacatg tagaaatgga caatggtcag aaccaccaaa atgcttacat    2880
ccgtgtgtaa tatcccgaga aattatggaa aattataaca tagcattaag gtggacagcc    2940
aaacagaagc tttattcgag aacaggtgaa tcagttgaat ttgtgtgtaa acggggatat    3000
cgtctttcat cacgttctca cacattgcga acaacatgtt gggatgggaa actggagtat    3060
ccaacttgtg caaaaagata ggcggccgcg tcgactgatc agcctcgact gtgccttcta    3120
gttgccagcc atctgttgtt tgcccctccc ccgtgccttc cttgaccctg gaaggtgcca    3180
ctcccactgt cctttcctaa taaaatgagg aaattgcatc gcattgtctg agtaggtgtc    3240
attctattct ggggggtggg gtggggcagg acagcaaggg ggaggattgg gaagacaaga    3300
tctaggaacc cctagtgatg gagttggcca ctccctctct gcgcgctcgc tcgctcactg    3360
aggccgcccg ggcaaagccc gggcgtcggg cgacctttgg tcgcccggcc tcagtgagcg    3420
agcgagcgcg cagagaggga gtggccaa                                       3448

<210> SEQ ID NO 9
<211> LENGTH: 286
<212> TYPE: DNA
<213> ORGANISM: Artificial Sequence
<220> FEATURE:
<223> OTHER INFORMATION: Synthetic Polynucleotide

<400> SEQUENCE: 9
tacggtaaat ggcccgcctg gctgaccgcc caacgacccc gcccattgac gtcaataatg     60
acgtatgttc ccatagtaac gccaataggg actttccatt gacgtcaatg ggtggagtat    120
ttacggtaaa ctgcccactt ggcagtacat caagtgtatc atatgccaag tacgccccct    180
attgacgtca atgacggtaa atggcccgcc tggcattatg cccagtacat gaccttatgg    240
gactttccta cttggcagta catctactcg aggccacgtt ctgctt                   286

<210> SEQ ID NO 10
<211> LENGTH: 493
<212> TYPE: DNA
<213> ORGANISM: Artificial Sequence
<220> FEATURE:
<223> OTHER INFORMATION: Synthetic Polynucleotide

<400> SEQUENCE: 10
tcaatattgg ccattagcca tattattcat tggttatata gcataaatca atattggcta     60
ttggccattg catacgttgt atctatatca taatatgtac atttatattg gctcatgtcc    120 aaatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg accccgccc attgacgtca ataatgacgt atgttcccat    300
```

-continued

```
agtaacgcca atagggactt tccattgacg tcaatgggtg gagtatttac ggtaaactgc      360
ccacttggca gtacatcaag tgtatcatat gccaagtccg cccctattg acgtcaatga       420 cggtaaatgg cccgcctggc attatgccca gtacatgacc ttacgggact ttcctacttg      480
gcagtacatc tac                                                        493
```

```
<210> SEQ ID NO 11
<211> LENGTH: 265
<212> TYPE: DNA
<213> ORGANISM: Artificial Sequence
<220> FEATURE:
<223> OTHER INFORMATION: Synthetic Polynucleotide

<400> SEQUENCE: 11
tctccccatc tccccccct ccccacccc aattttgtat ttatttattt tttaattatt        60
ttgtgcagcg atgggggcgg gggggggggg gggggggcg cgcgccaggc ggggcggggc      120
ggggcgaggg gcggggcggg gcgaggcgga gaggtgcggc ggcagccaat cagagcggcg     180
cgctccgaaa gtttcctttt atggcgaggc ggcggcggcg gcggccctat aaaaagcgaa     240
gcgcgcggcg ggcgggagcg ggatc                                          265
```

```
<210> SEQ ID NO 12
<211> LENGTH: 306
<212> TYPE: DNA
<213> ORGANISM: Artificial Sequence
<220> FEATURE:
<223> OTHER INFORMATION: Synthetic Polynucleotide

<400> SEQUENCE: 12
acgtattagt catcgctatt accatggtcg aggtgagccc cacgttctgc ttcactctcc       60
ccatctcccc ccctccca cccccaattt tgtatttatt tattttttaa ttattttgtg       120
cagcgatggg ggcgggggg ggggggggc gcgcgccagg cggggcgggg cggggcgagg      180
ggcggggcgg ggcgaggcgg agaggtgcgg cggcagccaa tcagagcggc gcgctccgaa     240 agtttcctttt tatggcgagg cggcggcggc ggcggcccta taaaaagcga agcgcgcggc     300
gggcgg                                                              306
```

```
<210> SEQ ID NO 13
<211> LENGTH: 172
<212> TYPE: DNA
<213> ORGANISM: Artificial Sequence
<220> FEATURE:
<223> OTHER INFORMATION: Synthetic Polynucleotide

<400> SEQUENCE: 13
gaactgaaaa accagaaagt taactggtaa gtttagtctt tttgtctttt atttcaggtc       60
ccggatccgg tggtggtgca aatcaaagaa ctgctcctca gtggatgttg cctttacttc      120
taggcctgta cggaagtgtt acttctgctc taaaagctgc ggaattgtac cc             172
```

```
<210> SEQ ID NO 14
<211> LENGTH: 1066
<212> TYPE: DNA
<213> ORGANISM: Artificial Sequence
<220> FEATURE:
<223> OTHER INFORMATION: Synthetic Polynucleotide

<400> SEQUENCE: 14
gagtcgctgc gcgctgcctt cgccccgtgc cccgctccgc cgccgcctcg cgccgcccgc       60
```

-continued

```
cccggctctg actgaccgcg ttactcccac aggtgagcgg gcgggacggc ccttctcctc      120
cgggctgtaa ttagcgcttg gtttaatgac ggcttgtttc ttttctgtgg ctgcgtgaaa      180
gccttgaggg gctccgggag ggcccttttgt gcgggggga gcggctcggg gggtgcgtgc      240
gtgtgtgtgt gcgtggggag cgccgcgtgc ggctccgcgc tgcccggcgg ctgtgagcgc      300
tgcgggcgcg gcgcggggct ttgtgcgctc cgcagtgtgc gcgaggggag cgcggccggg      360
ggcggtgccc cgcggtgcgg gggggctgc gaggggaaca aaggctgcgt gcggggtgtg       420
tgcgtggggg ggtgagcagg gggtgtgggc gcgtcggtcg ggctgcaacc cccctgcac      480 cccctcccc gagttgctga gcacggcccg gcttcgggtg cggggctccg tacggggcgt      540
ggcgcggggc tcgccgtgcc gggcgggggg tggcggcagg tgggggtgcc gggcgggcg      600 gggccgcctc gggccgggga gggctcgggg gaggggcgcg gcggccccg gagcgccggc     660 ggctgtcgag gcgcggcgag ccgcagccat tgccttttat ggtaatcgtg cgagagggcg      720
cagggacttc ctttgtccca aatctgtgcg gagccgaaat ctgggaggcg ccgccgcacc      780
ccctctagcg ggcgcggggc gaagcggtgc ggcgccggca ggaaggaaat gggcgggggag      840 ggccttcgtg cgtcgccgcg ccgccgtccc cttctccctc tccagcctcg gggctgtccg      900
cggggggacg gctgccttcg gggggacgg ggcagggcgg ggttcggctt ctggcgtgtg       960
accggcggct ctagagcctc tgctaaccat gttcatgcct tcttctttt cctacagctc     1020 ctgggcaacg tgctggttat tgtgctgtct catcattttg gcaaag                    1066
```

<210> SEQ ID NO 15
<211> LENGTH: 973
<212> TYPE: DNA
<213> ORGANISM: Artificial Sequence
<220> FEATURE:
<223> OTHER INFORMATION: Synthetic Polynucleotide

<400> SEQUENCE: 15

```
gtgagcgggc gggacggccc ttctcctccg ggctgtaatt agcgcttggt ttaatgacgg       60
cttgtttctt ttctgtggct gcgtgaaagc cttgaggggc tccgggaggg cccttttgtgc      120 ggggggagcg gctcggggggg tgcgtgcgtg tgtgtgtgcg tggggagcgc gcgtgcggc      180 tccgcgctgc ccggcggctg tgagcgctgc gggcgcggcg cggggctttg tgcgctccgc      240
agtgtgcgcg aggggagcgc ggccgggggc ggtgccccgc ggtgcggggg gggctgcgag      300
gggaacaaag gctgcgtgcg gggtgtgtgc gtggggggt gagcagggggg tgtgggcgcg      360 tcggtcgggc tgcaaccccc cctgcacccc cctccccgag ttgctgagca ggcccggct      420 tcgggtgcgg ggctccgtac ggggcgtggc gcggggctcg ccgtgccggg cgggggtgg      480 cggcaggtgg gggtgccggg cggggcgggg ccgcctcggg ccggggaggg ctcgggggag      540
gggcgcggcg gccccggag cgccggcggc tgtcgaggcg cggcgagccg cagccattgc      600 ctttttatggt aatcgtgcga gagggcgcag ggacttcctt tgtcccaaat ctgtgcggag      660
ccgaaatctg gaggcgccg ccgcacccc tctagcgggc gcggggcgaa gcggtgcggc       720
gccggcagga aggaaatggg cggggagggc cttcgtgcgt cgccgcgccg ccgtcccctt      780
ctccctctcc agcctcgggg ctgtccgcg ggggacggct gccttcgggg gggacggggc      840
agggcggggt tcggcttctg gcgtgtgacc ggcggctcta gagcctctgc taaccatgtt      900
catgccttct tctttttcct acagctcctg gcaacgtgc tggttattgt gctgtctcat      960
cattttggca aag                                                        973
```

-continued

```
<210> SEQ ID NO 16
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 16
ggccgctcca taaagtagga aacactacat ccataaagta ggaaacacta catccataaa      60
gtaggaaaca ctacagc                                                     77

<210> SEQ ID NO 17
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 17
ctcgactgtg ccttctagtt gccagccatc tgttgtttgc ccctcccccg tgccttcctt      60
gaccctggaa ggtgccactc ccactgtcct ttcctaataa aatgaggaaa ttgcatcgca     120
ttgtctgagt aggtgtcatt ctattctggg gggtggggtg gggcaggaca gcaaggggga     180
ggattgggaa gacaa                                                      195

<210> SEQ ID NO 18
<211> LENGTH: 127
<212> TYPE: DNA
<213> ORGANISM: Artificial Sequence
<220> FEATURE:
<223> OTHER INFORMATION: Synthetic Polynucleotide

<400> SEQUENCE: 18
gatctttttc cctctgccaa aaattatggg gacatcatga agccccttga gcatctgact      60
tctggctaat aaaggaaatt tattttcatt gcaatagtgt gttggaattt tttgtgtctc     120
tcactcg                                                              127

<210> SEQ ID NO 19
<211> LENGTH: 6
<212> TYPE: DNA
<213> ORGANISM: Artificial Sequence
<220> FEATURE:
<223> OTHER INFORMATION: Synthetic Polynucleotide

<400> SEQUENCE: 19 gccacc                                                                 6

<210> SEQ ID NO 20
<211> LENGTH: 4389
<212> TYPE: DNA
<213> ORGANISM: Artificial Sequence
<220> FEATURE:
<223> OTHER INFORMATION: Synthetic Polynucleotide

<400> SEQUENCE: 20
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaagaca ttgattattg actagttatt aatagtaatc     180
aattacgggg tcattagttc atagcccata tatggagttc cgcgttacat aacttacggt     240
aaatggcccg cctggctgac cgcccaacga cccccgccca ttgacgtcaa taatgacgta     300
```

-continued

```
tgttcccata gtaacgccaa tagggacttt ccattgacgt caatgggtgg actatttacg      360
gtaaactgcc cacttggcag tacatcaagt gtatcatatg ccaagtacgc cccctattga      420
cgtcaatgac ggtaaatggc ccgcctggca ttatgcccag tacatgacct tatgggactt      480
tcctacttgg cagtacatct acgtattagt catcgctatt accatgggtc gaggtgagcc      540
ccacgttctg cttcactctc cccatctccc cccctcccc  accccaatt  ttgtatttat      600 ttatttttta attattttgt gcagcgatgg gggcggggg  gggggggcg  cgcgccaggc      660 ggggcggggc ggggcgaggg gcggggcggg gcgaggcgga gaggtcggc  ggcagccaat      720 cagagcggcg cgctccgaaa gtttccttt  atggcgaggc ggcggcggcg gcggccctat      780
aaaaagcgaa gcgcgcggcg ggcgggagtc gctgcgttgc cttcgccccg tgccccgctc      840
cgcgccgcct cgcgccgccc gccccggctc tgactgaccg cgttactccc acaggtgagc      900
gggcgggacg gcccttctcc tccgggctgt aattagcgct tggtttaatg acggctcgtt      960
tcttttctgt ggctgcgtga aagccttaaa gggctccggg agggcccttt gtgcggggg     1020 gagcggctcg gggggtgcgt gcgtgtgtgt gtgcgtgggg agcgccgcgt gcggcccgcg    1080
ctgcccggcg gctgtgagcg ctgcgggcgc ggcgcggggc tttgtgcgct ccgcgtgtgc    1140
gcgaggggag cgcggccggg ggcggtgccc cgcggtgcgg gggggctgcg aggggaacaa    1200
aggctgcgtg cggggtgtgt gcgtgggggg gtgagcaggg ggtgtgggcg cggcggtcgg    1260
gctgtaaccc cccctgcac  cccctcccc  gagttgctga gcacggcccg gcttcgggtg    1320
cggggctccg tgcggggcgt ggcgcggggc tcgccgtgcc gggcggggg  tggcggcagg    1380 tgggggtgcc gggcggggcg gggccgcctc gggccgggga gggctcgggg gaggggcgcg    1440
gcggccccgg agcgccggcg gctgtcgagg cgcggcgagc cgcagccatt gccttttatg    1500
gtaatcgtgc gagagggcgc agggacttcc tttgtcccaa atctggcgga gccgaaatct    1560
gggaggcgcc gccgcacccc ctctagcggg cgcgggcgaa gcggtgcggc gccggcagga    1620
aggaaatggg cggggagggc cttcgtgcgt cgccgcgccg ccgtcccctt ctccatctcc    1680
agcctcgggg ctgccgcagg gggacggctg ccttcgggg  ggacggggca gggcgggtt    1740 cggcttctgg cgtgtgaccg gcggctctag agcctctgct aaccatgttc atgccttctt    1800 cttttttccta cagctcctgg gcaacgtgct ggttgttgtg ctgtctcatc attttggcaa    1860
agaattggac gttgtgaaca gagttagctg gtaaatgtcc tcttaaaaga tccaaaaaat    1920
gagacttcta gcaaagatta tttgccttat gttatgggct atttgtgtag cagaagattg    1980
caatgaactt cctccaagaa gaaatacaga aattctgaca ggttcctggt ctgaccaaac    2040
atatccagaa ggcacccagg ctatctataa atgccgccct ggatatagat ctcttggaaa    2100
tataataatg gtatgcagga agggagaatg ggttgctctt aatccattaa ggaaatgtca    2160
gaaaaggccc tgtggacatc ctggagatac tccttttggt acttttaccc ttacaggagg    2220
aaatgtgttt gaatatggtg taaaagctgt gtatacatgt aatgaggggt atcaattgct    2280
aggtgagatt aattaccgtg aatgtgacac agatggatgg accaatgata ttcctatatg    2340
tgaagttgtg aagtgtttac cagtgacagc accagagaat ggaaaaattg tcagtagtgc    2400
aatggaacca gatcgggaat accattttgg acaagcagta cggtttgtat gtaactcagg    2460
ctacaagatt gaaggagatg aagaaatgca ttgttcagac gatggttttt ggagtaaaga    2520
gaaaccaaag tgtgtggaaa tttcatgcaa atccccagat gttataaatg gatctcctat    2580
atctcagaag attatttata aggagaatga acgatttcaa tataaatgta acatgggtta    2640
tgaatacagt gaaagaggag atgctgtatg cactgaatct ggatggcgtc cgttgccttc    2700
```

-continued

```
atgtgaagaa aaatcaacct tgaaaccttg tgattatcca gacattaaac atggaggtct   2760
atatcatgag aatatgcgta gaccatactt tccagtagct gtaggaaaat attactccta   2820
ttactgtgat gaacattttg agactccgtc aggaagttac tgggatcaca ttcattgcac   2880
acaagatgga tggtcgccag cagtaccatg cctcagaaaa tgttattttc cttatttgga   2940
aaatggatat aatcaaaatt atggaagaaa gtttgtacag ggtaaatcta tagacgttgc   3000
ctgccatcct ggctacgctc ttccaaaagc gcagaccaca gttacatgta tggagaatgg   3060
ctggtctcct actcccagat gcatccgtgt caaaacatgt tccaaatcaa gtatagatat   3120
tgagaatggg tttatttctg aatctcagta tacatatgcc ttaaaagaaa aagcaaaata   3180
tcaatgcaaa ctaggatatg taacagcaga tggtgaaaca tcaggatcaa ttacatgtgg   3240
gaaagatgga tggtcagctc aacccacgtg cattaaatct ataaaaacag attgtctcag   3300
tttacctagc tttgaaaatg ccatacccat gggagagaag aaggatgtgt ataaggcggg   3360
tgagcaagtg acttacactt gtgcaacata ttacaaaatg gatggagcca gtaatgtaac   3420
atgcattaat agcagatgga caggaaggcc aacatgcaga gacacctcct gtgtgaatcc   3480
gcccacagta caaaatgctt atatagtgtc gagacagatg agtaaatatc catctggtga   3540
gagagtacgt tatcaatgta ggagcccctta tgaaatgttt ggggatgaag aagtgatgtg   3600
tttaaatgga aactggacgg aaccacctca atgcaaagat tctacaggaa aatgtgggcc   3660
ccctccacct attgacaatg gggacattac ttcattcccg ttgtcagtat atgctccagc   3720
ttcatcagtt gagtaccaat gccagaactt gtatcaactt gagggtaaca agcgaataac   3780
atgtagaaat ggacaatggt cagaaccacc aaaatgctta catccgtgtg taatatcccg   3840
agaaattatg gaaaattata acatagcatt aaggtggaca gccaaacaga agctttattc   3900
gagaacaggt gaatcagttg aatttgtgtg taaacgggga tatcgtcttt catcacgttc   3960
tcacacattg cgaacaacat gttgggatgg gaaactggag tatccaactt gtgcaaaaag   4020
atagaattca ctcctcaggt gcaggctgcc tatcagaagg tggtggctgg tgtggccaat   4080
gccctggctc acaaatacca ctgagatctt tttccctctg ccaaaaatta tggggacatc   4140
atgaagcccc ttgagcatct gacttctggc taataaagga aatttatttt cattgcaata   4200
gtgtgttgga attttttgtg tctctcactc ggaaggtggc gggttaatca ttaactacaa   4260 ggaacccta gtgatggagt tggccactcc ctctctgcgc gctcgctcgc tcactgaggc   4320
cgggcgacca aaggtcgccc gacgcccggg ctttgcccgg gcggcctcag tgagcgagcg   4380
agcgcgcag                                                            4389
```

FACTOR H VECTORS AND USES THEREOF

RELATED APPLICATION

This application is a national stage filing under 35 U.S.C. § 371 of international PCT application PCT/US2020/027452, filed Apr. 9, 2020, which claims priority under 35 U.S.C. § 119(e) to U.S. provisional patent application, U.S. Ser. No. 62/831,870, filed Apr. 10, 2019, the entire contents of each of which are incorporated herein by reference.

BACKGROUND

Factor H (FH) is a plasma regulator of the alternative pathway (AP) of complement activation, which inhibits complement activation both in the fluid phase and on the cell surface. Single nucleotide polymorphism and rare mutations in human FH are associated with age-related macular degeneration and severe kidney diseases including C3 glomerulopathy (C3G) and atypical hemolytic uremic syndrome.

SUMMARY

Aspects of the disclosure relate to compositions and methods for delivering Factor H (FH) to cells (e.g., cells of a subject). The disclosure is based, in part, on isolated nucleic acids (e.g., rAAV vectors) and rAAVs engineered to express transgenes encoding Factor H protein or variants thereof. In some embodiments, isolated nucleic acid and rAAVs described herein comprise one or more of the following structural features: a long Chicken Beta Actin (CBA) promoter, an extended CBA intron, a Kozak sequence, a codon-optimized human Factor H (hFH) protein variant-encoding nucleic acid sequence, one or more miR-142 binding sites (e.g., 1, 2, 3, 4, 5, or more miR-142 binding sites, etc.), and a rabbit beta-globulin (RBG) poly A sequence. In some embodiments, isolated nucleic acids and rAAVs described by the disclosure express increased (e.g., at least 2-fold, 3-fold, 4-fold, 5-fold, 10-fold, or more increased) levels of Factor H protein in a cell or subject compared to previously described AAV constructs engineered to express Factor H (e.g., a construct having the nucleic acid sequence set forth in SEQ ID NO: 20).

Accordingly, in some aspects, the disclosure provides an isolated nucleic acid comprising a transgene comprising a nucleic acid sequence encoding a Factor H protein variant having an amino acid sequence that is at least 70% identical to the amino acid sequence set forth in SEQ ID NO: 3 operably linked to a Kozak sequence (SEQ ID NO: 19).

In some embodiments, a Factor H protein variant comprises an amino acid sequence that is at least 80%, 90%, 99%, or 100% identical to the amino acid sequence set forth in SEQ ID NO: 3. In some embodiments, a Factor H protein variant consists of the amino acid sequence set forth in SEQ ID NO: 3.

In some embodiments, a nucleic acid sequence encoding a Factor H protein variant is at least 60%, 70%, 80%, 90%, 95%, 99%, or 99.9% identical to the nucleic acid sequence set forth in SEQ ID NO: 4.

In some embodiments, a transgene comprises a promoter operably linked to a nucleic acid sequence and/or the Kozak sequence. In some embodiments, a promoter comprises the sequence set forth in SEQ ID NO: 11 or 12. In some embodiments, a promoter further comprises an enhancer sequence. In some embodiments, an enhancer sequence comprises the sequence set forth in SEQ ID NO: 9 or 10. In some embodiments, a promoter comprises the sequences set forth in SEQ ID NOs: 9 and 11. In some embodiments, a promoter comprises the sequences set forth in SEQ ID NOs: 10 and 12.

In some embodiments, a transgene comprises one or more introns (e.g., one or more synthetic or artificial introns). In some embodiments, at least one intron of a transgene is positioned between a promoter and a nucleic acid sequence encoding a Factor H protein variant. In some embodiments, at least one intron comprises the sequence set forth in any one of SEQ ID NOs: 13-15.

In some embodiments, a transgene comprises a 3' untranslated region (3'UTR). In some embodiments, a 3'UTR comprises the sequence set forth in SEQ ID NO: 17 or 18.

In some embodiment, a transgene further comprises one or more miRNA binding sites. In some embodiments, one or more miRNA binding sites are positioned in a 3'UTR of the transgene. In some embodiments, at least one miRNA binding site is a miR-122 binding site. In some embodiments, at least one miRNA binding site is an immune-associated miRNA binding site. In some embodiments, an immune-associated miRNA is miR-142. In some embodiments, one or more miRNA binding sites comprise at least three miR-142 binding sites as set forth in SEQ ID NO: 16.

In some embodiments, a transgene is flanked by adeno-associated virus (AAV) inverted terminal repeats (ITRs), for example AAV2 ITRs.

In some embodiments, the disclosure provides an isolated nucleic acid comprising the sequence set forth in any one of SEQ ID NOs: 5-8.

In some embodiments, the disclosure provides a vector comprising an isolated nucleic acid as described herein. In some embodiments, a vector is a plasmid or a viral vector. In some embodiments, a viral vector is an adenoviral vector, adeno-associated virus vector, a lentiviral vector, a retroviral vector, or a Baculovirus vector.

In some aspects, the disclosure provides a composition comprising an isolated nucleic acid or a vector as described herein. In some embodiments, a pharmaceutical composition further comprises a pharmaceutically acceptable excipient.

In some embodiments, the disclosure provides a host cell comprising an isolated nucleic acid or a vector as described herein. In some embodiments, a host cell is a mammalian cell, yeast cell, bacterial cell, or insect cell.

In some aspects, the disclosure provides a recombinant adeno-associated virus (rAAV) comprising: (i) an isolated nucleic acid as described herein; and (ii) an adeno-associated virus (AAV) capsid protein.

In some embodiments, a capsid protein has a tropism for (e.g., specifically or preferentially targets) muscle tissue. In some embodiments, a capsid protein has a tropism for (e.g., specifically or preferentially targets) ocular tissue.

In some embodiments, a capsid protein is of a serotype selected from AAV1, AAV2, AAV3, AAV4, AAV5, AAV6, AAV7, AAV8, AAV9, AAV9.hr, AAVrh8, AAVrh10, AAVrh39, AAVrh43 and a variant of any of the foregoing.

In some aspects, the disclosure provides a method for increasing Factor H expression in a cell, the method comprising delivering to a cell an isolated nucleic acid, vector, composition, or rAAV as described herein.

In some embodiments, a cell is a mammalian cell. In some embodiments, a mammalian cell is a human cell. In some embodiments, a cell is a muscle cell or an ocular cell. In some embodiments, a cell is in a subject.

In some aspects, the disclosure provides a method for treating a disease associated with Factor H deficiency, the method comprising administering to a subject having a disease associated with Factor H deficiency an isolated nucleic acid, vector, composition, or rAAV as described herein.

In some embodiments, a subject is a mammal. In some embodiments, a subject is a human. In some embodiments, a subject is characterized by one or more mutations in a CFH gene. In some embodiments, one or more mutations of a CFH gene result in reduced expression and/or activity of Factor H protein in the subject relative to Factor H protein expression in a healthy subject (e.g., a subject that does not have one or more mutations in a CFH gene).

In some embodiments, a disease (e.g., a disease associated with Factor H deficiency) is C3 glomerulopathy (C3G) or atypical hemolytic uremic syndrome (aHUS). In some embodiments, a disease (e.g., a disease associated with Factor H deficiency) is age-related macular degeneration (AMD).

In some embodiments, an isolated nucleic acid, vector, composition, or rAAV is administered to a subject by systemic administration. In some embodiments, administration is intravenous injection.

In some embodiments, administration is direct administration to ocular tissue. In some embodiments, direct administration to ocular tissue is intraocular injection or topical administration.

In some embodiments, administration is intramuscular injection.

DETAILED DESCRIPTION

Figures 1A, 1B:
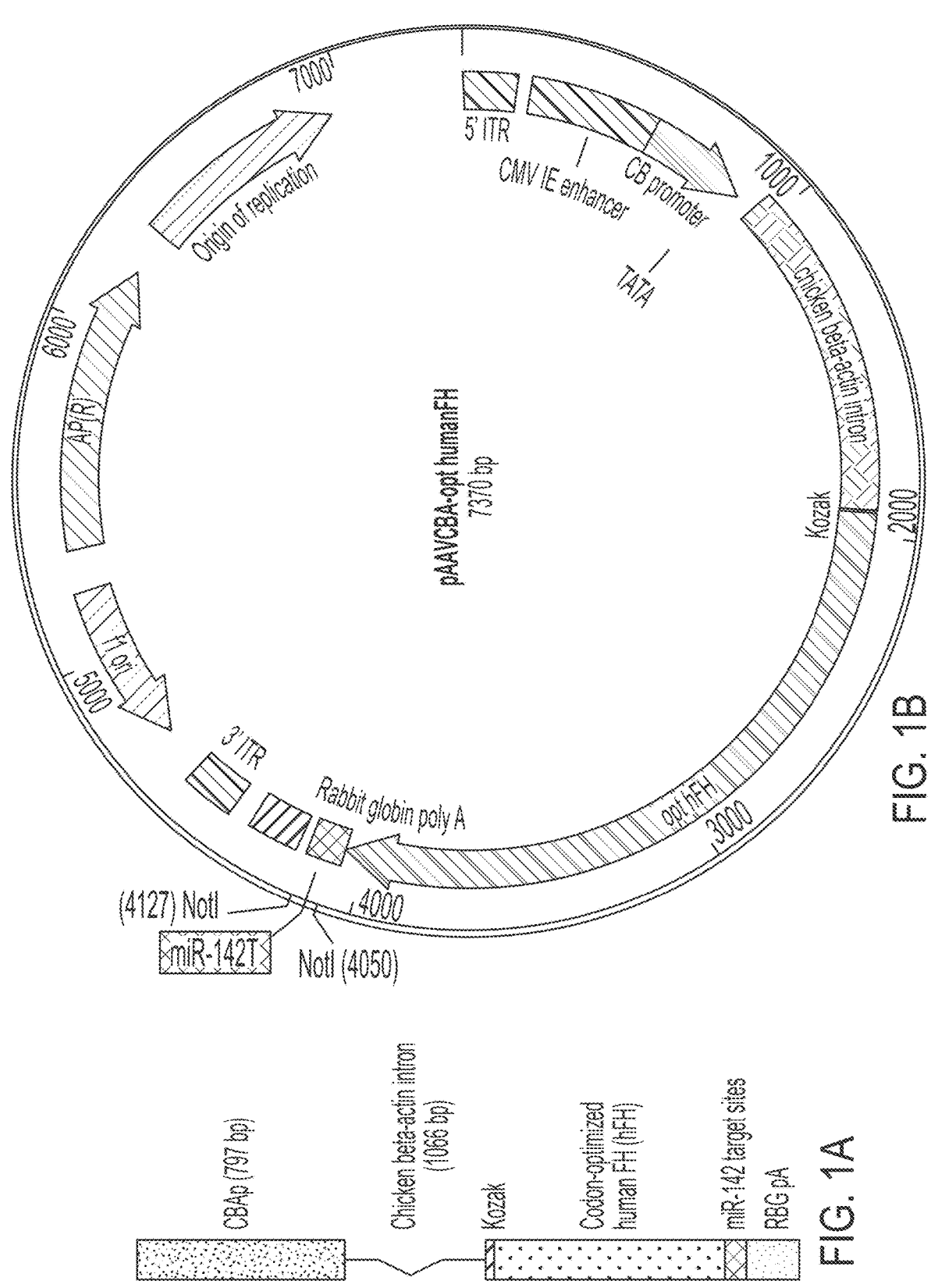
FIGS. 1A-1B show schematics depicting one embodiment of an rAAV vector encoding a codon-optimized human Factor H variant operably linked to a chicken-beta actin promoter and a chicken-beta actin intron (e.g., CAG promoter), and further comprising miR-142 binding sites. The vector also includes a rabbit beta-globulin polyA (RBG pA) region.

In some aspects, the disclosure relates to compositions and methods for delivering Factor H (FH) to cells (e.g., cells of a subject). The disclosure is based, in part, on isolated nucleic acids (e.g., rAAV vectors) and rAAVs engineered to express transgenes encoding Factor H protein or variants thereof.

Isolated Nucleic Acids

The disclosure relates, in some aspects, to isolated nucleic acids encoding a Factor H protein or a variant thereof. Factor H protein is a soluble glycoprotein member of the complement activation protein family. Without wishing to be bound by any particular theory, Factor H protein has been observed to play a role in regulating the alternative pathway of the immune complement system. In humans, Factor H is encoded by the CFH gene, from which two isoforms of Factor H protein are transcribed. Factor H "isoform a" comprises the amino acid sequence set forth in NCBI Accession Number NP_000177.2. Factor H "isoform b" comprises the amino acid sequence set forth in NCBI Accession Number NP_001014975.1. In some embodiments, a Factor H protein comprises the amino acid sequence set forth SEQ ID NO: 2 or is encoded by the nucleic acid sequence set forth in NCBI Accession Number NM_000186.3 or SEQ ID NO: 1. In some embodiments, a CFH gene encoding a Factor H protein is a codon-optimized CFH gene.

As used herein, a "Factor H protein variant" refers to protein that comprises one or more amino acid substitutions and/or amino acid deletions relative to a wild-type Factor H protein, such as a Factor H isoform a protein (e.g., a protein having the amino acid sequence set forth in SEQ ID NO: 2) or a Factor H isoform b protein. A Factor H protein variant may have an amino acid sequence that is at least 40%, at least 50%, at least 60%, at least 70%, at least 80%, at least 90%, at least 95%, or at least 99% identical to the amino acid sequence of a wild-type Factor H protein (e.g., a protein having the amino acid sequence set forth in SEQ ID NO: 2). A skilled artisan will recognize that the percentage identity of two sequences may be calculated by a variety of algorithms known in the art, for example by Basic Local Alignment (e.g., BLAST) or global multiple sequence alignment (e.g., CLUSTAL alignment methods).

In some embodiments, a Factor H protein variant comprises one or more (e.g., 1, 2, 3, 4, 5, 6, 7, 8, 9, 10, 20, 30, 40, 50, 60, 70, 80, 90, 100, or more) amino acid substitutions relative to a wild-type Factor H protein (e.g., a protein having the amino acid sequence set forth in SEQ ID NO: 2). In some embodiments, a nucleic acid sequence encoding a Factor H protein variant comprises one or more nucleic acid substitutions relative to a nucleic acid sequence encoding a wild-type Factor H protein (e.g., a nucleic acid having the nucleotide sequence set forth in SEQ ID NO: 1).

In some embodiments, a Factor H protein variant comprises one or more (e.g., 1, 2, 3, 4, 5, 6, 7, 8, 9, 10, 20, 30, 40, 50, 60, 70, 80, 90, 100, or more) amino acid deletions relative to a wild-type Factor H protein (e.g., a protein having the amino acid sequence set forth in SEQ ID NO: 2). In some embodiments, a Factor H protein variant comprises between 1 and 20 amino acid deletions relative to a wild-type Factor H protein (e.g., a protein having the amino acid sequence set forth in SEQ ID NO: 2). In some embodiments, a Factor H protein variant comprises between 10 and 50 amino acid deletions relative to a wild-type Factor H protein (e.g., a protein having the amino acid sequence set forth in SEQ ID NO: 2). In some embodiments, a Factor H protein variant comprises between 25 and 75 amino acid deletions relative to a wild-type Factor H protein (e.g., a protein having the amino acid sequence set forth in SEQ ID NO: 2). In some embodiments, a Factor H protein variant comprises between 50 and 200 amino acid deletions relative to a wild-type Factor H protein (e.g., a protein having the amino acid sequence set forth in SEQ ID NO: 2). In some embodiments, a Factor H protein variant comprises more than 200 (e.g., 250, 300, 400, or more) amino acid deletions relative to a wild-type Factor H protein (e.g., a protein having the amino acid sequence set forth in SEQ ID NO: 2). In some embodiments, a nucleic acid sequence encoding a Factor H protein variant comprises one or more nucleic acid substitutions relative to a nucleic acid sequence encoding a wild-type Factor H protein (e.g., a nucleic acid having the nucleotide sequence set forth in SEQ ID NO: 1). In some embodiments, a Factor H protein comprises or consists of the sequence set forth in SEQ ID NO: 3 or is encoded by a nucleic acid comprising or consisting of the sequence set forth in SEQ ID NO: 4.

In some embodiments, the nucleic acid sequence encoding a Factor H protein comprises at least 80%, at least 85%, at least 90%, at least 95%, at least 96%, at least 97%, at least 98%, or at least 99% identity to SEQ ID NO: 4. In some embodiments, the nucleic acid sequence encoding a Factor H protein comprises up to 20 nucleotides that are different from the nucleic acid sequence set forth in SEQ ID NO: 4. In some embodiments, the nucleic acid encoding a Factor H protein comprises 1, 2, 3, 4, 5, 6, 7, 8, 9, 10, 11, 12, 13, 14, 15, 16, 17, 18, 19, or 20 nucleotides that are different from the nucleic acid set forth in SEQ ID NO: 4. In some embodiments, the nucleic acid sequence encoding a Factor H protein comprises more than 20 nucleotides that are different from the nucleic acid set forth in SEQ ID NO: 4.

In some embodiments, the nucleic acid sequence encoding a Factor H protein comprises insertions relative to SEQ ID NO: 4. In some embodiments, the nucleic acid sequences encoding a Factor H protein comprises insertions relative to SEQ ID NO: 4 that do not introduce a frameshift mutation. In some embodiments, an insertion in the nucleic acid sequence relative to SEQ ID NO: 4 involves the insertion of multiples of 3 nucleotides (e.g., 3, 6, 9, 12, 15, 18, etc.). In some embodiments, an insertion in the nucleic acid sequence relative to SEQ ID NO: 4 leads to an increase in the total number of amino acid residues in the resultant Factor H protein (e.g., an increase of 1-3, 1-5, 3-10, 5-10, 5-15, or 10-20 amino acid residues).

In some embodiments, the nucleic acid sequence encoding a Factor H protein comprises deletions relative to SEQ ID NO: 4. In some embodiments, the nucleic acid sequences encoding a Factor H protein comprises deletions relative to SEQ ID NO: 4 that do not introduce a frameshift mutation. In some embodiments, an deletion in the nucleic acid sequence relative to SEQ ID NO: 4 involves the deletion of multiples of 3 nucleotides (e.g., 3, 6, 9, 12, 15, 18, etc.). In some embodiments, a deletion in the nucleic acid sequence relative to SEQ ID NO: 4 leads to an decrease in the total number of amino acid residues in the resultant Factor H protein (e.g., a decrease of 1-3, 1-5, 3-10, 5-10, 5-15, or 10-20 amino acid residues).

Aspects of the disclosure relate to codon-optimized nucleic acid sequences. In some embodiments, the nucleic acid sequence encoding Factor H protein is a codon-optimized sequence (e.g., codon optimized for expression in mammalian cells). Without wishing to be bound by any particular theory, codon-optimization enables the reduction of certain undesirable characteristics in nucleic acid sequences, for example structural elements that may be immunogenic in a mammalian host (e.g., CpG islands, high GC content, etc.). In some embodiments, a codon-optimized sequence encoding Factor H protein comprises reduced GC content relative to a wild-type sequence that has not been codon-optimized. In some embodiments, a codon-optimized sequence encoding Factor H protein comprises a 1-5%, 3-5%, 3-10%, 5-10%, 5-15%, 10-20%, 15-30%, 20-40%, 25-50%, or 30-60% reduction in GC content relative to a wild-type sequence that has not been codon-optimized. In some embodiments, a codon-optimized sequence encoding Factor H protein comprises fewer guanine and/or cytosine nucleobases relative to a wild-type sequence that has not been codon-optimized. In some embodiments, a codon-optimized sequence encoding Factor H protein comprises 1-5, 3-5, 3-10, 5-10, 5-15, 10-20, 15-30, 20-40, 25-50, or 30-60 fewer guanine and/or cytosine nucleobases relative to a wild-type sequence that has not been codon-optimized. In some embodiments, a codon-optimized sequence encoding Factor H protein comprises fewer CpG dinucleotide islands relative to a wild-type sequence that has not been codon-optimized. In some embodiments, a codon-optimized sequence encoding Factor H protein comprises 1-3, 3-5, 3-10, 5-10, 5-15, 10-20, 15-30, 20-40, 25-50, or 30-60 fewer CpG dinucleotide islands relative to a wild-type sequence that has not been codon-optimized.

In some embodiments, a Factor H protein variant comprising one or more amino acid substitutions or deletions relative to a wild-type Factor H protein retains its function (e.g., the protein variant retains the ability to regulate complement activity).

A "nucleic acid" sequence refers to a DNA or RNA sequence. In some embodiments, proteins and nucleic acids of the disclosure are isolated. As used herein, the term "isolated" means artificially produced. As used herein, with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

In some aspects, the disclosure relates to isolated nucleic acids comprising certain regulatory sequences which result in increased Factor H expression in cells relative to Factor H expression by previously described Factor H encoding constructs (e.g., having a sequence set forth in SEQ ID NO: 20). Expression of Factor H by isolated nucleic acids and constructs described herein may be increased at least 2-fold, 3-fold, 4-fold, 5-fold, 6-fold, 7-fold, 8-fold, 9-fold, 10-fold, or more (e.g., at least 20-fold, 50-fold, 100-fold, etc. relative to expression in by previously described Factor H encoding constructs (e.g., having a sequence set forth in SEQ ID NO: 20).

In some embodiments, isolated nucleic acid and rAAVs described herein comprise one or more of the following structural features (e.g., control or regulatory sequences): a long Chicken Beta Actin (CBA) promoter, an extended CBA intron, a Kozak sequence, a codon-optimized human Factor H (hFH) protein variant-encoding nucleic acid sequence, one or more miR-142 binding sites, and a rabbit beta-globulin (RBG) poly A sequence. In some embodiments, one or more of the foregoing control sequences is operably linked to a nucleic acid sequence encoding a Factor H protein or Factor H protein variant.

As used herein, a nucleic acid sequence (e.g., coding sequence) and regulatory sequences are said to be "operably linked" when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame.

In some embodiments, a transgene comprises a nucleic acid sequence encoding a Factor H protein or Factor H protein variant operably linked to a promoter. A "promoter" refers to a DNA sequence recognized by the synthetic machinery of the cell, or introduced synthetic machinery, required to initiate the specific transcription of a gene. The phrases "operatively linked," "operatively positioned," "under control" or "under transcriptional control" means that the promoter is in the correct location and orientation in relation to the nucleic acid to control RNA polymerase initiation and expression of the gene.

Generally, a promoter can be a constitutive promoter, inducible promoter, or a tissue-specific promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an RNA pol II promoter. In some embodiments, a promoter is an RNA pol III promoter, such as U6 or H1. In some embodiments, a promoter is an RNA pol II promoter.

Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene (e.g., Factor H, CFH) will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: retinoschisin proximal promoter, interphotoreceptor retinoid-binding protein enhancer (RS/IRBPa), rhodopsin kinase (RK), liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (α-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, the tissue-specific promoter is a liver-specific promoter, or an eye-specific promoter. Examples of liver-specific promoter include P1 promoter, P2 promoter, P3 promoter, P4 promoter, and thyroxin binding globulin (TBG) promoter. Examples of eye-specific promoters include retinoschisin proximal promoter, interphotoreceptor retinoid-binding protein enhancer (RS/IRBPa), rhodopsin kinase (RK), RPE65, and human cone opsin promoter.

In some embodiments, a promoter is a chicken beta-actin (CB) promoter. A chicken beta-actin promoter may be a short chicken beta-actin promoter (e.g., having the sequence set forth in SEQ ID NO: 9) or a long chicken beta-actin promoter (e.g., having the sequence set forth in SEQ ID NO: 11). In some embodiments, a promoter (e.g., a chicken beta-actin promoter) comprises an enhancer sequence, for example a cytomegalovirus (CMV) enhancer sequence. A CMV enhancer sequence may be a short CMV enhancer sequence (e.g., having the sequence set forth in SEQ ID NO: 10) or a long CMV enhancer sequence (e.g., having the sequence set forth in SEQ ID NO: 12). In some embodiments, a promoter comprises a long CMV enhancer sequence and a long chicken beta-actin promoter (e.g., SEQ ID NOs: 10 and 12). In some embodiments, a promoter comprises a short CMV enhancer sequence and a short chicken beta-actin promoter (e.g., SEQ ID NOs: 10 and 12). However, the skilled artisan recognizes that a short CMV enhancer may be used with a long CB promoter, and a long CMV enhancer may be used with a short CB promoter (and vice versa).

An isolated nucleic acid described herein may also contain an intron, desirably located between the promoter/enhancer sequence and the transgene. In some embodiments, an intron is a synthetic or artificial (e.g., heterologous) intron. Examples of synthetic introns include an intron sequence derived from SV-40 (referred to as the SV-40 T intron sequence) and intron sequences derived from chicken beta-actin gene. In some embodiments, a transgene described by the disclosure comprises one or more (1, 2, 3, 4, 5, or more) artificial introns. In some embodiments, the one or more artificial introns are positioned between a promoter and a nucleic acid sequence encoding a Factor H protein or Factor H protein variant. In some embodiments, the one or more introns each independently comprise a sequence selected from SEQ ID NOs: 13-15.

In some embodiments, the rAAV comprises a posttranscriptional response element. As used herein, the term "posttranscriptional response element" refers to a nucleic acid sequence that, when transcribed, adopts a tertiary structure that enhances expression of a gene. Examples of posttranscriptional regulatory elements include, but are not limited to, woodchuck hepatitis virus posttranscriptional regulatory element (WPRE), mouse RNA transport element (RTE), constitutive transport element (CTE) of the simian retrovirus type 1 (SRV-1), the CTE from the Mason-Pfizer monkey virus (MPMV), and the 5' untranslated region of the human heat shock protein 70 (Hsp70 5'UTR). In some embodiments, the rAAV vector comprises a woodchuck hepatitis virus posttranscriptional regulatory element (WPRE).

In some embodiments, the vector further comprises conventional control elements which are operably linked with elements of the transgene in a manner that permits its transcription, translation and/or expression in a cell transfected with the vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

A polyadenylation sequence generally is inserted following the transgene sequences and optionally before a 3' AAV ITR sequence. A rAAV construct useful in the disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989].

In some embodiments, a transgene comprises a poly A sequence is a rabbit beta-globulin (RBG) poly A sequence, for example as set forth in SEQ ID NO: 18.

In some embodiments, a transgene comprises a Kozak sequence. A Kozak sequence is a nucleic acid motif comprising a consensus sequence GCC(A/G)CC that is found in eukaryotic mRNA and plays a role in initiation of protein translation.

In some aspects, the disclosure relates to isolated nucleic acids comprising a transgene encoding a Factor H protein or Factor H protein variant, and one or more miRNA binding sites. Without wishing to be bound by any particular theory, incorporation of miRNA binding sites into gene expression constructs allows for regulation of transgene expression (e.g., inhibition of transgene expression) in cells and tissues where the corresponding miRNA is expressed. In some embodiments, incorporation of one or more miRNA binding sites into a transgene allows for de-targeting of transgene expression in a cell-type specific manner. In some embodiments, one or more miRNA binding sites are positioned in a 3' untranslated region (3' UTR) of a transgene, for example between the last codon of a nucleic acid sequence encoding a Factor H protein or variant thereof, and a poly A sequence.

In some embodiments, a transgene comprises one or more (e.g., 1, 2, 3, 4, 5, or more) miRNA binding sites that de-target expression of Factor H from liver cells. For example, in some embodiments, a transgene comprises one or more miR-122 binding sites. In some embodiments, a transgene comprises one or more miR-142 binding sites.

In some embodiments, a transgene comprises one or more (e.g., 1, 2, 3, 4, 5, or more) miRNA binding sites that de-target expression of Factor H from immune cells (e.g., antigen presenting cells (APCs), such as macrophages, dendrites, etc.). Incorporation of miRNA binding sites for immune-associated miRNAs may de-target transgene (e.g., Factor H) expression of Factor H from antigen presenting cells and thus reduce or eliminate immune responses (cellular and/or humoral) produced in the subject against products of the transgene, for example as described in US 2018/0066279, the entire contents of which are incorporated herein by reference.

As used herein an "immune-associated miRNA" is an miRNA preferentially expressed in a cell of the immune system, such as an antigen presenting cell (APC). In some embodiments, an immune-associated miRNA is an miRNA expressed in immune cells that exhibits at least a 2-fold, 3-fold, 4-fold, 5-fold, 6-fold, 7-fold, 8-fold, 9-fold, 10-fold higher level of expression in an immune cell compared with a non-immune cell (e.g., a control cell, such as a HeLa cell, HEK293 cell, mesenchymal cell, etc.). In some embodiments, the cell of the immune system (immune cell) in which the immune-associated miRNA is expressed is a B cell, T cell, Killer T cell, Helper T cell, γδ T cell, dendritic cell, macrophage, monocyte, vascular endothelial cell. or other immune cell. In some embodiments, the cell of the immune system is a B cell expressing one or more of the following markers: B220, BLAST-2 (EBVCS), Bu-1, CD19, CD20 (L26), CD22, CD24, CD27, CD57, CD72, CD79a, CD79b, CD86, chB6, D8/17, FMC7, L26, M17, MUM-1, Pax-5 (BSAP), and PC47H. In some embodiments, the cell of the immune system is a T cell expressing one or more of the following markers: ART2, CD1a, CD1d, CD11b (Mac-1), CD134 (OX40), CD150, CD2, CD25 (interleukin 2 receptor alpha), CD3, CD38, CD4, CD45RO, CD5, CD7, CD72, CD8, CRTAM, FOXP3, FT2, GPCA, HLA-DR, HML-1, HT23A, Leu-22, Ly-2, Ly-m22, MICG, MRC OX 8, MRC OX-22, OX40, PD-1 (Programmed death-1), RT6, TCR (T cell receptor), Thy-1 (CD90), and TSA-2 (Thymic shared Ag-2). In some embodiments, the immune-associated miRNA is selected from: miR-15a, miR-16-1, miR-17, miR-18a, miR-19a, miR-19b-1, miR-20a, miR-21, miR-29a/b/c, miR-30b, miR-31, miR-34a, miR-92a-1, miR-106a, miR-125a/b, miR-142-3p, miR-146a, miR-150, miR-155, miR-181a, miR-223 and miR-424, miR-221, miR-222, let-7i, miR-148, and miR-152. In some embodiments, a transgene described herein comprises one or more binding sites for miR-142, for example as set forth in SEQ ID NO: 16.

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid further comprises a region (e.g., a second region, a third region, a fourth region, etc.) comprising a second AAV ITR. In some embodiments, an isolated nucleic acid encoding a transgene is flanked by AAV ITRs (e.g., in the orientation 5'-ITR-transgene-ITR-3'). In some embodiments, the AAV ITRs are AAV2 ITRs.

Recombinant Adeno-Associated Viruses (rAAVs)

In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s) (e.g., ocular tissues, neurons). The AAV capsid is an important element in determining these tissue-specific targeting capabilities (e.g., tissue tropism). Thus, an rAAV having a capsid appropriate for the tissue being targeted can be selected.

In some embodiments, rAAVs of the disclosure comprise a nucleotide sequence as set forth in any one of SEQ ID NOs: 5-8 or encode a protein having an amino acid sequence as set forth in SEQ ID NO: 4. In some embodiments, rAAVs of the disclosure comprise a nucleotide sequence that is 99% identical, 95% identical, 90% identical, 85% identical, 80% identical, 75% identical, 70% identical, 65% identical, 60% identical, 55% identical, or 50% identical to a nucleotide sequence as set forth in SEQ ID NOs: 5-8.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein has a tropism for ocular tissues or muscle tissue. In some embodiments, an AAV capsid protein targets ocular cell types (e.g., photoreceptor cells, retinal cells, etc.). In some embodiments, an AAV capsid protein targets muscle cell types (e.g., myoblasts, myocytes, sarcomeres, etc.).

In some embodiments, an AAV capsid protein is of an AAV serotype selected from the group consisting of AAV1, AAV2, AAV3, AAV4, AAV5, AAV6, AAV7, AAV8, AAV9, AAV9.hr, AAVrh8, AAVrh10, AAVrh39, AAVrh43, AAV.PHP, and variants of any of the foregoing. In some embodiments, an AAV capsid protein is of a serotype derived from a non-human primate, for example AAVrh8 serotype. In some embodiments, the capsid protein is of AAV serotype 6, AAV serotype 8 (e.g., AAV8 capsid protein), AAV serotype 2 (e.g., AAV2 capsid protein), AAV serotype 5 (e.g., AAV5 capsid protein), or AAV serotype 9 (e.g., AAV9 capsid protein).

In some embodiments, an rAAV vector or rAAV particle comprises a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) Molecular Therapy 16(10):1648-1656.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the disclosure relates to a host cell containing a nucleic acid that comprises a coding sequence encoding a transgene (e.g., Factor H or a variant thereof). A "host cell" refers to any cell that harbors, or is capable of harboring, a substance of interest. Often a host cell is a mammalian cell. In some embodiments, a host cell is a neuron. In some embodiments, a host cell is a photoreceptor cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. In some embodiments, the host cell is a mammalian cell, a yeast cell, a bacterial cell, an insect cell, a plant cell, or a fungal cell. In some embodiments, the host cell is a neuron, a photoreceptor cell, a pigmented retinal epithelial cell, or a glial cell.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an AAV vector (comprising a transgene flanked by ITR elements) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpes virus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. In some embodiments, a vector is a viral vector, such as an rAAV vector, a lentiviral vector, an adenoviral vector, a retroviral vector, etc. Thus, the term includes cloning and expression vehicles, as well as viral vectors. In some embodiments, useful vectors are contemplated to be those vectors in which the nucleic acid segment to be transcribed is positioned under the transcriptional control of a promoter.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the disclosure relates to a kit for producing a rAAV, the kit comprising a container housing an isolated nucleic acid encoding a Factor H protein or a portion thereof. In some embodiments, the kit further comprises instructions for producing the rAAV. In some embodiments, the kit further comprises at least one container housing a recombinant AAV vector, wherein the recombinant AAV vector comprises a transgene.

In some embodiments, the disclosure relates to a kit comprising a container housing a recombinant AAV as described supra. In some embodiments, the kit further comprises a container housing a pharmaceutically acceptable carrier. For example, a kit may comprise one container housing a rAAV and a second container housing a buffer suitable for injection of the rAAV into a subject. In some embodiments, the container is a syringe.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

AAV-Mediated Delivery

The isolated nucleic acids, rAAVs, and compositions of the disclosure may be delivered to a subject in compositions according to any appropriate methods known in the art. For example, an rAAV, preferably suspended in a physiologically compatible carrier (e.g., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intraocular injection, subretinal injection, or by injection into the eye of the mammalian subject to ocular tissues. As used herein, "ocular tissues" refers to any tissue derived from or contained in the eye. Non-limiting examples of ocular tissues include neurons, retina (e.g., photoreceptor cells), sclera, choroid, retina, vitreous body, macula, fovea, optic disc, lens, pupil, iris, aqueous fluid, cornea, conjunctiva ciliary body, and optic nerve. The retina is located in the posterior of the eye and comprises photoreceptor cells. These photoreceptor cells (e.g., rods, cones) confer visual acuity by discerning color, as well as contrast in the visual field.

Alternatively, delivery of the rAAVs to a mammalian subject may be by intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. In some embodiments, an rAAV as described in the disclosure is administered by intraocular injection. In some embodiments, an rAAV as described in the disclosure is administered by subretinal injection. In some embodiments, an rAAV as described in the disclosure is administered by intravenous injection.

Aspects of the instant disclosure relate to compositions comprising a recombinant AAV comprising a capsid protein and a nucleic acid encoding a transgene, wherein the transgene comprises a nucleic acid sequence encoding a Factor H protein or a Factor H protein variant. In some embodiments, the nucleic acid further comprises AAV ITRs. In some embodiments, a composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, parachlorophenol, and poloxamers (non-ionic surfactants) such as Pluronic® F-68. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), intraocular injection, subretinal injection, oral, inhalation (including intranasal and intratracheal delivery), intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue (e.g., muscle tissue, ocular tissue, etc.). In some embodiments, an effective amount of an rAAV is administered to the subject during a pre-symptomatic stage of degenerative disease. In some embodiments, a subject is administered an rAAV or composition after exhibiting one or more signs or symptoms of degenerative disease. In some embodiments, an effective amount of an rAAV ranges between $1 \times 10^9$ and $1 \times 10^{14}$ genome copies of the rAAV.

An effective amount of an rAAV may also depend on the mode of administration. For example, targeting an ocular (e.g., corneal) tissue by intrastromal administration or subcutaneous injection may require different (e.g., higher or lower) doses, in some cases, than targeting an ocular (e.g., corneal) tissue by another method (e.g., systemic administration, topical administration). In some embodiments, intrastromal injection (IS) of rAAV having certain serotypes (e.g., AAV2, AAV5, AAV6, AAV6.2, AAV7, AAV8, AAV9, AAVrh.8, AAVrh.10, AAVrh.39, and AAVrh.43) mediates efficient transduction of ocular (e.g., corneal, retinal, etc.) cells. Thus, in some embodiments, the injection is intrastromal injection (IS). In some embodiments, the injection is topical administration (e.g., topical administration to an eye). In some cases, multiple doses of a rAAV are administered.

In some embodiments, rAAV compositions are formulated to reduce aggregation of AAV particles in the composition, particularly where high rAAV concentrations are present (e.g., $\sim 10^{13}$ GC/mL or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either intraocularly, subretinally, subcutaneously, intraopancreatically, intranasally, parenterally, intravenously, intramuscularly, intrathecally, orally, intraperitoneally, or by inhalation. In some embodiments, the administration modalities as described in U.S. Pat. Nos. 5,543,158; 5,641,515 and 5,399, 363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuumdrying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Methods of Treating Diseases Associated with Factor H Deficiency

Aspects of the disclosure relate to methods for delivering a transgene encoding Factor H protein or a Factor H protein variant to a cell (e.g., a cell in a subject). In some embodiments, methods described by the disclosure are useful for treating a subject having or suspected of having a disease associated with Factor H deficiency. As used herein, "Factor H deficiency" refers to the reduced expression or activity of Factor H protein in a subject relative to a healthy subject (e.g., a subject characterized by normal expression or activity of Factor H protein). In some embodiments, a subject having a Factor H deficiency is characterized by a level of expression or activity of Factor H that is at least 1%, 5%, 10%, 20%, 50%, 75%, or 100% (e.g., no expression of Factor H) less than a healthy subject. In some embodiments, a subject having a Factor H deficiency is characterized by a level of expression or activity of Factor H that is at least 2-fold, 5-fold, 10-fold, 50-fold, 100-fold, or more less than a healthy subject. Examples of diseases associated with Factor H deficiency include age-related macular degeneration (AMD), C3 glomerulopathy (C3G), and atypical hemolytic uremic syndrome (aHUS).

A subject may be a human, a mouse, a rat, a pig, a dog, a cat, or a non-human primate. In some embodiments, a subject has or is suspected of having a disease or disorder associated with Factor H deficiency (e.g., age-related macular degeneration (AMD), C3 glomerulopathy (C3G), and atypical hemolytic uremic syndrome (aHUS)).

In some aspects, the disclosure provides a method of promoting expression of functional Factor H protein in a subject comprising administering the isolated nucleic acids, the rAAVs, or the compositions described herein to a subject having or suspected of having a disease of disorder associated with Factor H deficiency (e.g., age-related macular degeneration (AMD), C3 glomerulopathy (C3G), and atypical hemolytic uremic syndrome (aHUS)). As used herein, a disease of disorder associated with Factor H deficiency is a disease or disorder in which a subject has at least 10%, at least 20%, at least 30%, at least 40%, at least 50%, at least 60%, at least 70%, at least 80%, or at least 90% lower levels of Factor H expression relative to a control subject (e.g., a healthy subject or an untreated subject).

In some embodiments, administering the isolated nucleic acids, the rAAVs, or the compositions described herein to a subject promotes expression of Factor H by between 2-fold and 100-fold (e.g., 2-fold, 5-fold, 10-fold, 20-fold, 50-fold, 75-fold, 100-fold, etc.) compared to a control subject. In some embodiments, administering the isolated nucleic acids, the rAAVs, or the compositions described herein to a subject promotes expression of Factor H in a subject by between 2-fold and 100-fold (e.g., 2-fold, 5-fold, 10-fold, 20-fold, 50-fold, 75-fold, 100-fold, etc.) compared to a control subject. As used herein a "control" subject may refer to a subject that is not administered the isolated nucleic acids, the rAAVs, or the compositions described herein; or a healthy subject. In some embodiments, a control subject is the same subject that is administered the isolated nucleic acids, the rAAVs, or the compositions described herein (e.g., prior to the administration). In some embodiments, administering the isolated nucleic acids, the rAAVs, or the compositions described to a subject promotes expression of Factor H by 2-fold compared to a control. In some embodiments, administering the isolated nucleic acids, the rAAVs, or the compositions described to a subject promotes expression of Factor H by 100-fold compared to a control. In some embodiments, administering the isolated nucleic acids, the rAAVs, or the compositions described to a subject promotes expression of Factor H by 5-fold compared to a control. In some embodiments, administering the isolated nucleic acids, the rAAVs, or the compositions described to a subject promotes expression of Factor H by 10-fold compared to a control. In some embodiments, administering the isolated nucleic acids, the rAAVs, or the compositions described to a subject promotes expression of Factor H by 5-fold to 100-fold compared to control (e.g., 5-fold to 10-fold, 10-fold to 15-fold, 10-fold to 20-fold, 15-fold to 25-fold, 20-fold to 30-fold, 25-fold to 35-fold, 30-fold to 40-fold, 35-fold to 45-fold, 40-fold to 60-fold, 50-fold to 75-fold, 60-fold to 80-fold, 75-fold to 100-fold compared to a control).

In some embodiments, administering the isolated nucleic acids, the rAAVs, or the compositions described herein to a subject promotes expression of Factor H in a subject (e.g., promotes expression of Factor H in a subject) by between a 5% and 200% increase (e.g., 5-50%, 25-75%, 50-100%, 75-125%, 100-200%, or 100-150% etc.) compared to a control subject.

As used herein, the term "treating" refers to the application or administration of a composition comprising Factor H protein or a variant thereof to a subject, who has a disease associated with Factor H deficiency, a symptom of a disease associated with Factor H deficiency, or a predisposition toward a disease associated with Factor H deficiency (e.g., one or more mutations in the CFH gene), with the purpose to cure, heal, alleviate, relieve, alter, remedy, ameliorate, improve, or affect the disorder, the symptom of the disease, or the predisposition toward a disease associated with Factor H deficiency.

Alleviating a disease associated with Factor H deficiency includes delaying the development or progression of the disease, or reducing disease severity. Alleviating the disease does not necessarily require curative results. As used therein, "delaying" the development of a disease (such as a disease associated with Factor H deficiency) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease associated with Factor H deficiency includes initial onset and/or recurrence.

EXAMPLES

Example 1

Compared to a previously described AAV vector encoding Factor H protein, rAAV constructs described in this Example include one or more of the following features: a long Chicken Beta Actin (CBA) promoter (e.g., SEQ ID NO: 10), extended CBA intron (e.g., SEQ ID NO: 12), a Kozak sequence (e.g., SEQ ID NO: 19), a nucleic acid encoding a codon-optimized human Factor H (hFH) protein variant (e.g., a codon-optimized sequence encoding the amino acid sequence set forth in SEQ ID NO: 3, or a nucleic acid comprising the sequence set forth in SEQ ID NO: 4), one or more miR-142 binding sites (e.g., SEQ ID NO: 16) and a rabbit beta-globulin (RBG) poly A sequence (e.g. SEQ ID NO: 18).

Figures 2A, 2B:
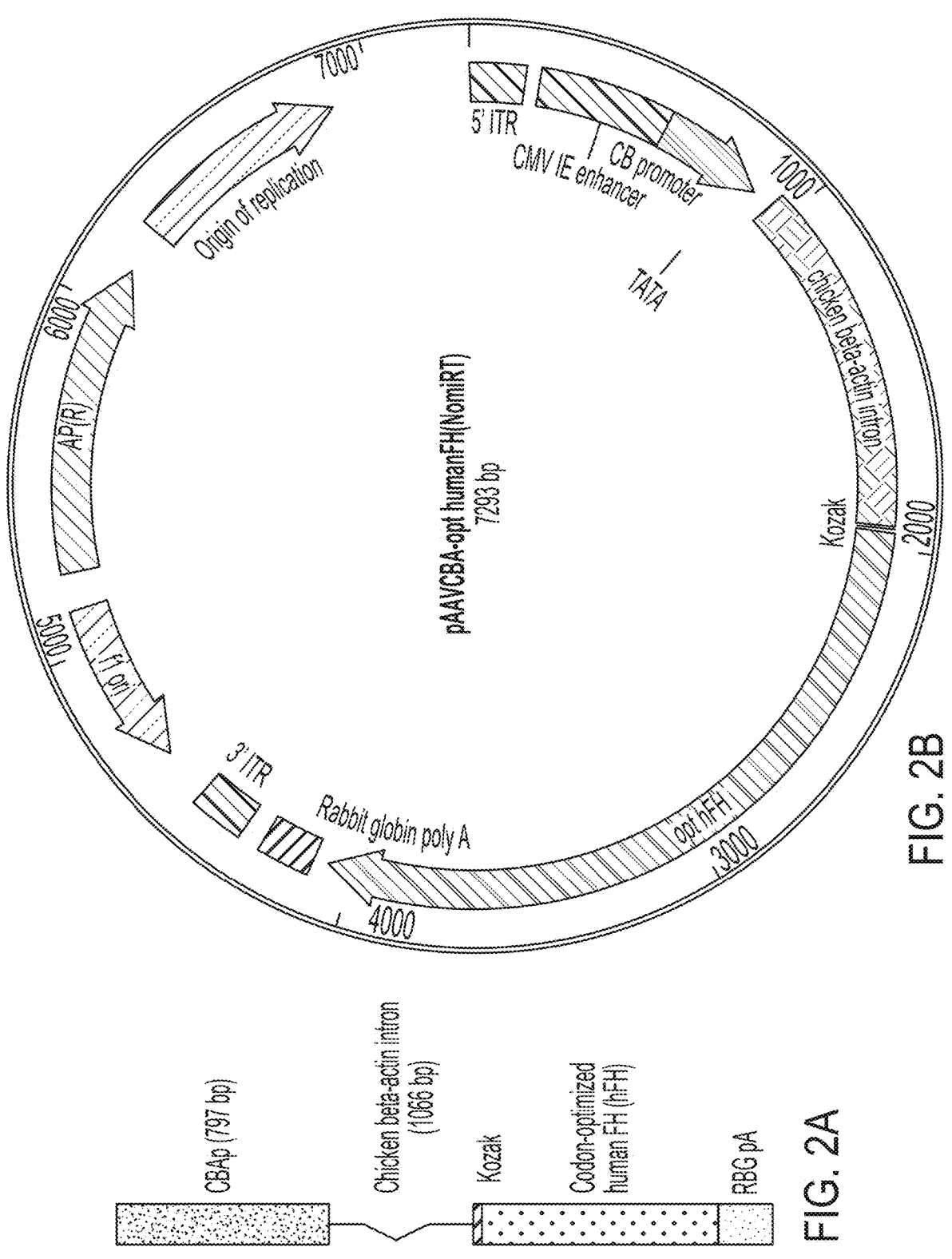
FIGS. 2A-2B show schematics depicting one embodiment of an rAAV vector encoding a codon-optimized human Factor H variant operably linked to a chicken-beta actin promoter and a chicken-beta actin intron (e.g., CAG promoter). The vector also includes a rabbit beta-globulin polyA (RBG pA) region.
Figures 3A, 3B:
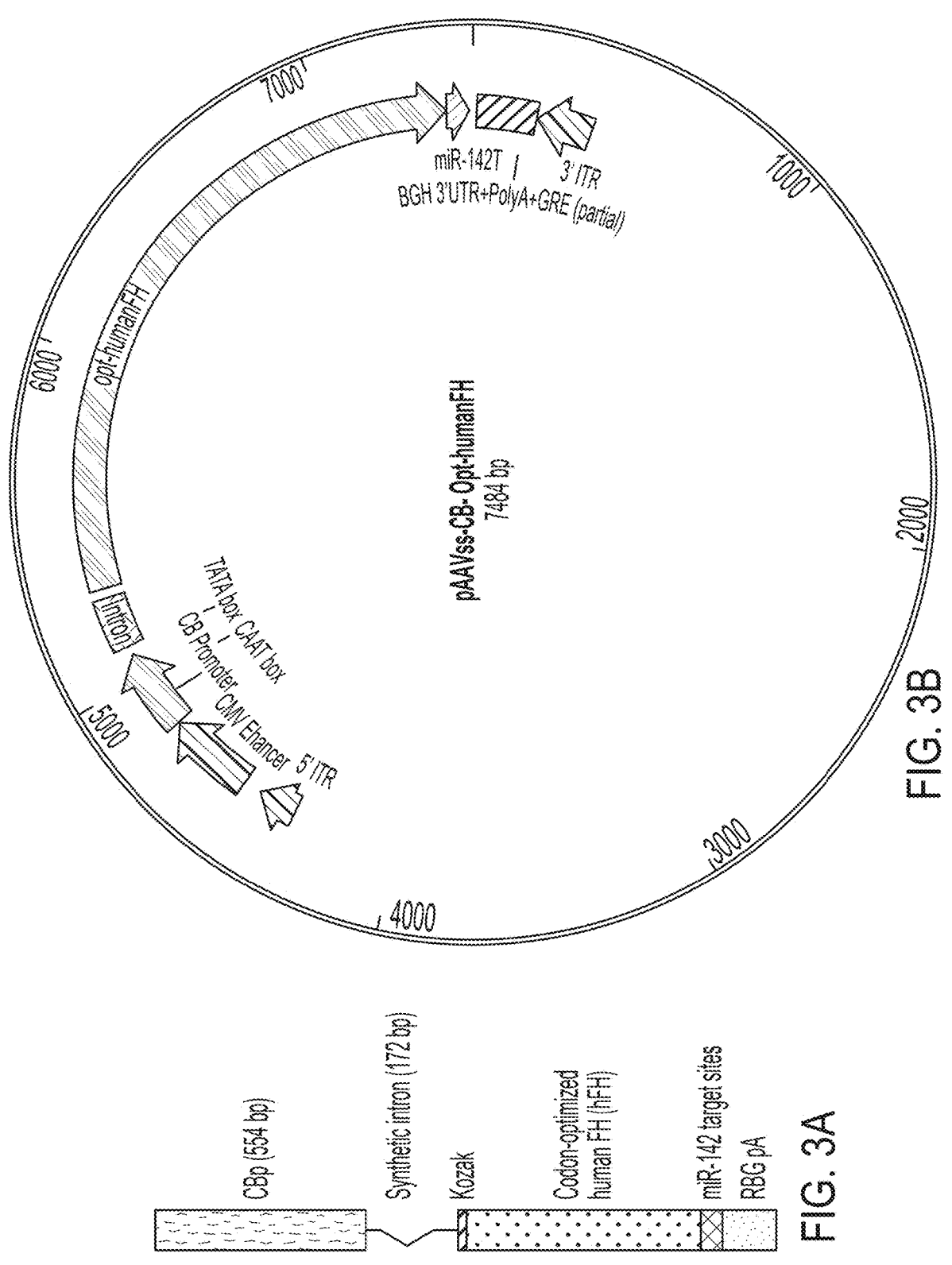
FIGS. 3A-3B show schematics depicting one embodiment of an rAAV vector encoding a codon-optimized human Factor H variant operably linked to a chicken-beta actin promoter, a synthetic intron, and a Kozak sequence. The vector also includes miR-142 binding sites and a rabbit beta-globulin polyA (RBG pA) region.
Figures 4A, 4B:
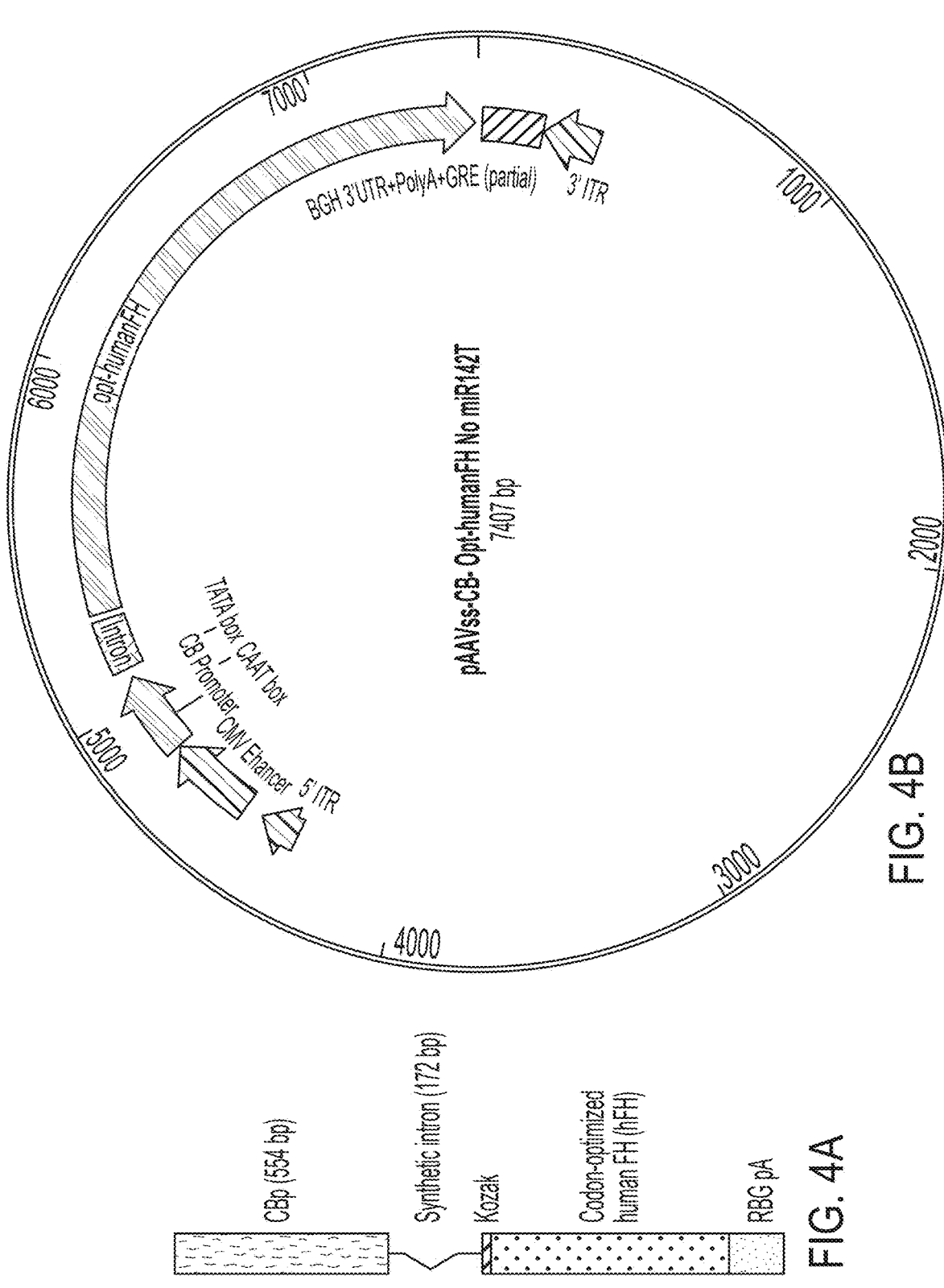
FIGS. 4A-4B show schematics depicting one embodiment of an rAAV vector encoding a codon-optimized human Factor H variant operably linked to a chicken-beta actin promoter, a synthetic intron, and a Kozak sequence. The vector also includes a rabbit beta-globulin polyA (RBG pA) region.

Examples of constructs described by the disclosure are shown in FIGS. 1A-4B and in SEQ ID NOs: 5-8.

The pAAVCBA-opt-humanFH construct (FIG. 1A-1B) comprises the CBA promoter, the extended CBA intron, a Kozak sequence, a codon-optimized sequence encoding hFH, miR-142 binding sites in the in the 3' untranslated region (UTR), and a RBG polyA sequence.

The pAAVCBA-opt-humanFH(No-miRT) construct (FIG. 2A-2B) comprises the CBA promoter, the extended CBA intron, a Kozak sequence, a codon-optimized sequence encoding hFH, and a RBG polyA sequence.

The pAAVss-CB-opt-humanFH construct (FIG. 3A-3B) comprises the CBA promoter, a synthetic intron, a Kozak sequence, a codon-optimized sequence encoding hFH, miR-142 binding sites in the in the 3' untranslated region (UTR), and a RBG polyA sequence.

The pAAVss-CB-opt-humanFH(No-miRT) construct (FIG. 4A-4B) comprises the CBA promoter, a synthetic intron, a Kozak sequence, a codon-optimized sequence encoding hFH, and a RBG polyA sequence.

A mouse model of C3 glomerulopathy was systemically injected (via hydrodynamic injection) with rAAV particles shown in Table 1. Factor H expression was measured one week post-administration. It was observed that injection of Factor H-encoding rAAV vectors described by the disclosure resulted in a ~five-fold increase in Factor H expression compared to injection of a previously described Factor H-encoding vector (e.g., SEQ ID NO: 20) in mice. Table 1 provides a summary of the vector yield, FH expression from hydrodynamic injected vectors in the mice.

TABLE 1

| Vectors | Vector yield (one prep) | Hydrodynamic injection (24 h) | AAV expression (weekl) |
|---|---|---|---|
| pAAV Original CBA-hFH | 1.7 × E13 GC | ~0.18 μM | ~320 nM |
| pAAVss-CB-Opt-humanFH | 3.8 × E13 GC | ~0.20 μM | ~50 nM |
| pAAVss-CB-Opt-humanFH (NomiRT) | 3.6 × E13 GC | ~0.20 μM | ~50 nM |
| pAAV CBA-Opt-humanFH | 1.5 × E13 GC | ~0.13 μM | ~1700 nM |
| pAAV CBA-Opt-humanFH (NomiRT) | | | |

Example 2

A non-human primate model (e.g., non-human primate model of C3 glomerulopathy) is systemically injected (via hydrodynamic injection) with rAAV constructs of the disclosure that comprise a codon-optimized sequence encoding hFH (set forth in SEQ ID NO: 4). The tested rAAV constructs are: (1) pAAVCBA-opt-humanFH construct; (2) pAAVCBA-opt-humanFH(No-miRT) construct; (3) pAAVss-CB-opt-humanFH construct; and pAAVss-CB-opt-humanFH(No-miRT) construct. A control rAAV that had been previously described (pAAV Original CBA-hFH, set forth in SEQ ID NO: 20) is also tested.

After administration of the rAAV constructs, Factor H protein expression in the serum and tissues of the non-human primates is measured (e.g., on a daily or weekly basis), using standard protein techniques (e.g., western blotting). The expression level of Factor H protein provides an indicator of transgene expression stability. Furthermore, the immune responses of the primates to the rAAVs are determined. The primates are observed for a period of time (e.g., days, weeks, or months) and phenotypic measurements are collected (e.g., mortality/moribundity of the primates, body weight, food consumption). Pathology examinations in main organs (e.g., liver, kidney, pancreas, spleen, muscle, heart, lung, brain, and gonads etc.) are performed following the death of a primate or at the conclusion of the study.

```
SEQUENCES
>Human Factor H nucleic acid coding sequence
                                                              (SEQ ID NO: 1)
ATGAGACTTCTAGCAAAGATTATTTGCCTTATGTTATGGGCTATTTGTGTAGCAGAAGATTG

CAATGAACTTCCTCCAAGAAGAAATACAGAAATTCTGACAGGTTCCTGGTCTGACCAAACA
```

-continued

```
TATCCAGAAGGCACCCAGGCTATCTATAAATGCCGCCCTGGATATAGATCTCTTGGAAATAT

AATAATGGTATGCAGGAAGGGAGAATGGGTTGCTCTTAATCCATTAAGGAAATGTCAGAAA

AGGCCCTGTGGACATCCTGGAGATACTCCTTTTGGTACTTTTACCCTTACAGGAGGAAATGT

GTTTGAATATGGTGTAAAAGCTGTGTATACATGTAATGAGGGGTATCAATTGCTAGGTGAGA

TTAATTACCGTGAATGTGACACAGATGGATGGACCAATGATATTCCTATATGTGAAGTTGTG

AAGTGTTTACCAGTGACAGCACCAGAGAATGGAAAAATTGTCAGTAGTGCAATGGAACCAG

ATCGGGAATACCATTTTGGACAAGCAGTACGGTTTGTATGTAACTCAGGCTACAAGATTGAA

GGAGATGAAGAAATGCATTGTTCAGACGATGGTTTTTGGAGTAAAGAGAAACCAAAGTGTG

TGGAAATTTCATGCAAATCCCCAGATGTTATAAATGGATCTCCTATATCTCAGAAGATTATT

TATAAGGAGAATGAACGATTTCAATATAAATGTAACATGGGTTATGAATACAGTGAAAGAG

GAGATGCTGTATGCACTGAATCTGGATGGCGTCCGTTGCCTTCATGTGAAGAAAAATCATGT

GATAATCCTTATATTCCAAATGGTGACTACTCACCTTTAAGGATTAAACACAGAACTGGAGA

TGAAATCACGTACCAGTGTAGAAATGGTTTTTATCCTGCAACCCGGGGAAATACAGCCAAA

TGCACAAGTACTGGCTGGATACCTGCTCCGAGATGTACCTTGAAACCTTGTGATTATCCAGA

CATTAAACATGGAGGTCTATATCATGAGAATATGCGTAGACCATACTTTCCAGTAGCTGTAG

GAAAATATTACTCCTATTACTGTGATGAACATTTTGAGACTCCGTCAGGAAGTTACTGGGAT

CACATTCATTGCACACAAGATGGATGGTCGCCAGCAGTACCATGCCTCAGAAAATGTTATTT

TCCTTATTTGGAAAATGGATATAATCAAAATTATGGAAGAAAGTTTGTACAGGGTAAATCTA

TAGACGTTGCCTGCCATCCTGGCTACGCTCTTCCAAAAGCGCAGACCACAGTTACATGTATG

GAGAATGGCTGGTCTCCTACTCCCAGATGCATCCGTGTCAAAACATGTTCCAAATCAAGTAT

AGATATTGAGAATGGGTTTATTTCTGAATCTCAGTATACATATGCCTTAAAAGAAAAAGCAA

AATATCAATGCAAACTAGGATATGTAACAGCAGATGGTGAAACATCAGGATCAATTACATG

TGGGAAAGATGGATGGTCAGCTCAACCCACGTGCATTAAATCTTGTGATATCCCAGTATTTA

TGAATGCCAGAACTAAAAATGACTTCACATGGTTTAAGCTGAATGACACATTGGACTATGA

ATGCCATGATGGTTATGAAAGCAATACTGGAAGCACCACTGGTTCCATAGTGTGTGGTTACA

ATGGTTGGTCTGATTTACCCATATGTTATGAAAGAGAATGCGAACTTCCTAAAATAGATGTA

CACTTAGTTCCTGATCGCAAGAAAGACCAGTATAAAGTTGGAGAGGTGTTGAAATTCTCCTG

CAAACCAGGATTTACAATAGTTGGACCTAATTCCGTTCAGTGCTACCACTTTGGATTGTCTC

CTGACCTCCCAATATGTAAAGAGCAAGTACAATCATGTGGTCCACCTCCTGAACTCCTCAAT

GGGAATGTTAAGGAAAAAACGAAAGAAGAATATGGACACAGTGAAGTGGTGGAATATTAT

TGCAATCCTAGATTTCTAATGAAGGGACCTAATAAAATTCAATGTGTTGATGGAGAGTGGAC

AACTTTACCAGTGTGTATTGTGGAGGAGAGTACCTGTGGAGATATACCTGAACTTGAACATG

GCTGGGCCCAGCTTTCTTCCCCTCCTTATTACTATGGAGATTCAGTGGAATTCAATTGCTCAG

AATCATTTACAATGATTGGACACAGATCAATTACGTGTATTCATGGAGTATGGACCCAACTT

CCCCAGTGTGTGGCAATAGATAAACTTAAGAAGTGCAAATCATCAAATTTAATTATACTTGA

GGAACATTTAAAAAACAAGAAGGAATTCGATCATAATTCTAACATAAGGTACAGATGTAGA

GGAAAAGAAGGATGGATACACACAGTCTGCATAAATGGAAGATGGGATCCAGAAGTGAAC

TGCTCAATGGCACAAATACAATTATGCCCACCTCCACCTCAGATTCCCAATTCTCACAATAT

GACAACCACACTGAATTATCGGGATGGAGAAAAAGTATCTGTTCTTTGCCAAGAAAATTAT

CTAATTCAGGAAGGAGAAGAAATTACATGCAAAGATGGAAGATGGCAGTCAATACCACTCT
```

-continued

GTGTTGAAAAAATTCCATGTTCACAACCACCTCAGATAGAACACGGAACCATTAATTCATCC

AGGTCTTCACAAGAAAGTTATGCACATGGGACTAAATTGAGTTATACTTGTGAGGGTGGTTT

CAGGATATCTGAAGAAAATGAAACAACATGCTACATGGGAAAATGGAGTTCTCCACCTCAG

TGTGAAGGCCTTCCTTGTAAATCTCCACCTGAGATTTCTCATGGTGTTGTAGCTCACATGTCA

GACAGTTATCAGTATGGAGAAGAAGTTACGTACAAATGTTTTGAAGGTTTTGGAATTGATGG

GCCTGCAATTGCAAAATGCTTAGGAGAAAAATGGTCTCACCCTCCATCATGCATAAAAACA

GATTGTCTCAGTTTACCTAGCTTTGAAAATGCCATACCCATGGGAGAGAAGAAGGATGTGTA

TAAGGCGGGTGAGCAAGTGACTTACACTTGTGCAACATATTACAAAATGGATGGAGCCAGT

AATGTAACATGCATTAATAGCAGATGGACAGGAAGGCCAACATGCAGAGACACCTCCTGTG

TGAATCCGCCCACAGTACAAAATGCTTATATAGTGTCGAGACAGATGAGTAAATATCCATCT

GGTGAGAGAGTACGTTATCAATGTAGGAGCCCTTATGAAATGTTTGGGGATGAAGAAGTGA

TGTGTTTAAATGGAAACTGGACGGAACCACCTCAATGCAAAGATTCTACAGGAAAATGTGG

GCCCCCTCCACCTATTGACAATGGGGACATTACTTCATTCCCGTTGTCAGTATATGCTCCAGC

TTCATCAGTTGAGTACCAATGCCAGAACTTGTATCAACTTGAGGGTAACAAGCGAATAACAT

GTAGAAATGGACAATGGTCAGAACCACCAAAATGCTTACATCCGTGTGTAATATCCCGAGA

AATTATGGAAAATTATAACATAGCATTAAGGTGGACAGCCAAACAGAAGCTTTATTCGAGA

ACAGGTGAATCAGTTGAATTTGTGTGTAAACGGGGATATCGTCTTTCATCACGTTCTCACAC

ATTGCGAACAACATGTTGGGATGGGAAACTGGAGTATCCAACTTGTGCAAAAGATA

>Human Factor H amino acid sequence (SEQ ID NO: 2)

MRLLAKIICLMLWAICVAEDCNELPPRRNTEILTGSWSDQTYPEGTQAIYKCRPGYRSLGNIIMV

CRKGEWVALNPLRKCQKRPCGHPGDTPFGTFTLTGGNVFEYGVKAVYTCNEGYQLLGEINYRE

CDTDGWTNDIPICEVVKCLPVTAPENGKIVSSAMEPDREYHFGQAVRFVCNSGYKIEGDEEMHC

SDDGFWSKEKPKCVEISCKSPDVINGSPISQKIIYKENERFQYKCNMGYEYSERGDAVCTESGWR

PLPSCEEKSCDNPYIPNGDYSPLRIKHRTGDEITYQCRNGFYPATRGNTAKCTSTGWIPAPRCTLK

PCDYPDIKHGGLYHENMRRPYFPVAVGKYYSYYCDEHFETPSGSYWDHIHCTQDGWSPAVPCL

RKCYFPYLENGYNQNYGRKFVQGKSIDVACHPGYALPKAQTTVTCMENGWSPTPRCIRVKTCS

KSSIDIENGFISESQYTYALKEKAKYQCKLGYVTADGETSGSITCGKDGWSAQPTCIKSCDIPVFM

NARTKNDFTWFKLNDTLDYECHDGYESNTGSTTGSIVCGYNGWSDLPICYERECELPKIDVHLV

PDRKKDQYKVGEVLKFSCKPGFTIVGPNSVQCYHFGLSPDLPICKEQVQSCGPPPELLNGNVKEK

TKEEYGHSEVVEYYCNPRFLMKGPNKIQCVDGEWTTLPVCIVEESTCGDIPELEHGWAQLSSPP

YYYGDSVEFNCSESFTMIGHRSITCIHGVWTQLPQCVAIDKLKKCKSSNLIILEEHLKNKKEFDHN

SNIRYRCRGKEGWIHTVCINGRWDPEVNCSMAQIQLCPPPPQIPNSHNMTTTLNYRDGEKVSVL

CQENYLIQEGEEITCKDGRWQSIPLCVEKIPCSQPPQIEHGTINSSRSSQESYAHGTKLSYTCEGGF

RISEENETTCYMGKWSSPPQCEGLPCKSPPEISHGVVAHMSDSYQYGEEVTYKCFEGFGIDGPAI

AKCLGEKWSHPPSCIKTDCLSLPSFENAIPMGEKKDVYKAGEQVTYTCATYYKMDGASNVTCIN

SRWTGRPTCRDTSCVNPPTVQNAYIVSRQMSKYPSGERVRYQCRSPYEMFGDEEVMCLNGNWT

EPPQCKDSTGKCGPPPPIDNGDITSFPLSVYAPASSVEYQCQNLYQLEGNKRITCRNGQWSEPPK

CLHPCVISREIMENYNIALRWTAKQKLYSRTGESVEFVCKRGYRLSSRSHTLRTTCWDGKLEYP

TCAKR

-continued

>Engineered Human Factor H amino acid sequence (SEQ ID NO: 3)

MRLLAKIICLMLWAICVAEDCNELPPRRNTEILTGSWSDQTYPEGTQAIYKCRPGYRSLGNIIMV

CRKGEWVALNPLRKCQKRPCGHPGDTPFGTFTLTGGNVFEYGVKAVYTCNEGYQLLGEINYRE

CDTDGWTNDIPICEVVKCLPVTAPENGKIVSSAMEPDREYHFGQAVRFVCNSGYKIEGDEEMHC

SDDGFWSKEKPKCVEISCKSPDVINGSPISQKIIYKENERFQYKCNMGYEYSERGDAVCTESGWR

PLPSCEEKSTLKPCDYPDIKHGGLYHENMRRPYFPVAVGKYYSYYCDEHFETPSGSYWDHIHCT

QDGWSPAVPCLRKCYFPYLENGYNQNYGRKFVQGKSIDVACHPGYALPKAQTTVTCMENGWS

PTPRCIRVKTCSKSSIDIENGFISESQYTYALKEKAKYQCKLGYVTADGETSGSITCGKDGWSAQP

TCIKSIKTDCLSLPSFENAIPMGEKKDVYKAGEQVTYTCATYYKMDGASNVTCINSRWTGRPTC

RDTSCVNPPTVQNAYIVSRQMSKYPSGERVRYQCRSPYEMFGDEEVMCLNGNWTEPPQCKDST

GKCGPPPPIDNGDITSFPLSVYAPASSVEYQCQNLYQLEGNKRITCRNGQWSEPPKCLHPCVISRE

IMENYNIALRWTAKQKLYSRTGESVEFVCKRGYRLSSRSHTLRTTCWDGKLEYPTCAKR

>Engineered Human Factor H codon-optimized nucleic acid sequence (SEQ ID NO: 4)

atgagacttctagcaaagattatttgccttatgttatgggctatttgtgtagcagaagattgcaatgaacttcctccaagaagaaatacagaaatt ctgacaggttcctggtctgacccaaacatatccagaaggcaccccaggctatctatataaatgccgccctggatatagatctcttggaaatataataatg gtatgcaggaagggagaatgggttgctcttaatccattaaggaaatgtcagaaaaggcccctgtggacatcctggagatactcctttttggtactttt acccttacaggaggaaatgtgtttgaatatggtgtaaaagctgtgtatacatgtaatgaggggtatcaattgctaggtgagattaattaccgtgaa tgtgacacagatggatggaccaatgatattcctatatgtgaagttgtgaagtgtttaccagtgacagcaccagagaatggaaaaattgtcagtagt gcaatggaaccagatcgggaataccattttggacaagcagtacggtttgtatgtaactcaggctacaagattgaaggagatgaagaaatgcattgt tcagacgatggttttttggagtaaagagaaaccaaagtgtgtggaaatttcatgcaaatccccagatgttataaatggatctcctatatctcagaag attatttataaggagaatgaacgatttcaatataaatgtaacatgggttatgaatacagtgaaagaggagatgctgtatgcactgaatctggatgg cgtccgttgccttcatgtgaagaaaaatcaaccttgaaaccttgtgattatccagacattaaacatggaggtctatatcatgagaatatgcgtaga ccatactttccagtagctgtaggaaaatattactcctattactgtgatgaacattttgagactccgtcaggaagttactgggatcacattcattgc acacaagatggatggtcgccagcagtaccatgcctcagaaaatgttatttttccttatttggaaaatggatataatcaaaattatggaagaaagtttt gtacagggtaaatctatagacgttgcctgccatcctggctacgctcttccaaaagcgcagacacagttacatgtatggagaatggctggtctcct actcccagatgcatccgtgtcaaaacatgttccaaatcaagtatagatattgagaatgggtttatttctgaatctcagtatacatatgccttaaaa gaaaaagcaaaatatcaatgcaaactaggatatgtaacagcagatggtgaaacatcaggatcaattacatgtgggaaagatggatggtcagctcaa cccacgtgcattaaatctataaaaacagattgtctcagtttacctagctttgaaaatgccatacccatgggagagaagaaggatgtgtataaggcg ggtgagcaagtgacttacacttgtgcaacatattacaaaatggatggagccagtaatgtaacatgcattaatagcagatggacaggaaggccaaca tgcagagacacctcctgtgtgaatccgcccacagtacaaaatgcttatatagtgtcgagacagatgagtaaatatccatctggtgagagagtacgt tatcaatgtaggagcccttatgaaatgtttggggatgaagaagtgatgtgtgtttaaatggaaactggacggaaccacctcaatgcaaagattctaca ggaaaatgtgggcccctccacctattgacaatgggggacattacttcattcccgttgtcagtatatgctccagcttcatcagttgagtaccaatgc cagaacttgtatcaacttgagggtaacaagcgaataacatgtagaaatggacaatggtcagaaccaccaaaatgcttacatccgtgtgtaatatcc cgagaaattatggaaaattataacatagcattaaggtggacagccaaacagaagctttattcgagaacaggtgaatcagttgaatttgtgtgtaaa cggggatatcgtctttcatcacgttctcacacacattgcgaacaacatgttgggatgggaaactggagtatccaacttgtgcaaaaagatag >pAAVCBA-Opt-humanFH rAAV vector nucleic acid sequence (SEQ ID NO: 5)

ctgcgcgctcgctcgctcactgaggccgcccgggcaaagcccgggcgtcgggcgacctttggtcgcccggcctcagtgagcgagcgagcgcgcaga gagggagtggccaactccatcactaggggttccttgtagttaatgattaacccgccatgctacttatctaccagggtaatgggggatcctctagaac tatagctagtcgacattgattattgactagttattaatagtaatcaattacggggtcattagttcatagcccatatatggagttccgcgttacata acttacggtaaatggcccgcctggctgaccgcccaacgacccccgcccattgacgtcaataatgacgtatgttcccatagtaacgccaatagggac -continued

```
tttccattgacgtcaatgggtggagtatttacggtaaactgcccacttggcagtacatcaagtgtatcatatgccaagtacgccccctattgacgt caatgacggtaaatggcccgcctggcattatgcccagtacatgaccttatgggactttcctacttggcagtacatctacgtattagtcatcgctat taccatggtcgaggtgagccccacgttctgcttcactctccccatctcccccccctccccacccccaattttgtatttatttattttttaattatt ttgtgcagcgatgggggcggggggggggggggggcgcgcgccaggcggggcggggcggggcgaggggcggggcggggcgaggcggagaggtgcggc ggcagccaatcagagcggcgcgctccgaaagtttccttttatggcgaggcggcggcggcggcggccctataaaaagcgaagcgcgcggcgggcggg gagtcgctgcgacgctgccttcgccccgtgccccgctccgccgccgcctcgcgccgcccgcccccggctctgactgaccgcgttactcccacaggtg agcgggcgggacggcccttctcctccgggctgtaattagcgcttggtttaatgacggcttgtttcttttctgtggctgcgtgaaagccttgagggg ctccgggagggccctttgtgcggggggagcggctcggggggtgcgtgcgtgtgtgtgtgcgtggggagcgccgcgtgcggctccgcgctgcccggc ggctgtgagcgctgcgggcgcggcgcggggctttgtgcgctccgcagtgtgcgcgaggggagcgcggccggggcggtgccccgcggtgcggggggg ggctgcgaggggaacaaaggctgcgtgcggggtgtgtgcgtgggggggtgagcaggggtgtgggcgcgtcggtcgggctgcaacccccccctgcac ccccctccccgagttgctgagcacggcccggcttcgggtgcggggctccgtacggggcgtggcgcggggctcgccgtgccgggcgggggggtggcgg caggtgggggtgccgggcggggcggggccgcctcgggccggggagggctcggggagggcgcggcggcccccggagcgccggcggctgtcgaggc gcggcgagccgcagccattgccttttatggtaatcgtgcgagagggcgcaggacttcctttgtcccaaatctgtgcggagccgaaatctgggagg cgccgccgcaccccctctagcgggcgcggggcgaagcggtgcggcgccggcaggaaggaaatgggcggggagggccttcgtgcgtcgccgcgccgc cgtcccttctccctctccagcctcggggctgtccgcgggggacggctgccttcggggggacggggcagggcggggttcggcttctggcgtgtg accggcggctctagagcctctgctaaccatgttcatgccttcttcttttttcctacagctcctgggcaacgtgctggttattgtgctgtctcatcat tttggcaaagaattcgccaccatgcgcctgctggccaagatcatctgcctgatgctgtgggccatctgcgtggccgaggactgtaacgagctgccc cctcggagaaatacagagatcctgaccggctcttggagcgatcagacctacccagagggcacacaggccatctacaagtgcaggcccggctatcgc tccctgggcaatatcatcatggtgtgcaggaagggagagtgggtggccctgaacccactgagaaagtgccagaagaggccatgtggacacccaggc gacacacctttcggcacctttacactgaccggcggcaacgtgttcgagtacggcgtgaaggccgtgtataacctgcaatgagggctaccagctgctg ggcgagatcaactaccgggagtgtgacacagatggctggaccaatgatatccccatctgcgaggtggtgaagtgtctgccagtgaccgcccccgag aacggcaagatcgtgagctccgccatggagcctgacagagagtatcacttcggccaggccgtgaggttcgtgtgcaatagcggctacaagatcgag ggcgatgaggagatgcactgttccgacgatggcttctggtctaaggagaagcccaagtgcgtggagatctcctgtaagtctcctgacgtgattaac ggcagcccaatctcccagaagatcatctataaggagaatgagcggtttcagtacaagtgcaacatgggctacgagtattccgagagaggcgatgcc gtgtgcacagagtctggatggaggcccctgcctagctgcgaggagaagtccaccctgaagccttgtgactatccagatatcaagcacggcggcctg tatcacgagaatatgaggcgcccttacttcccagtggccgtgggcaagtactattcctactattgcgacgagcactttgagacaccatccggctct tactgggaccacatccactgtacccaggatggctggtctcccgccgtgccttgcctgagaaagtgttacttcccctatctggagaacggctacaac cagaattatggcaggaagtttgtgcagggcaagtccatcgacgtggcatgccacccaggatacgcactgcctaaggcacagaccacagtgacctgt atggagaatggctggagcccaacacccaggtgcatccgcgtgaagacctgttccaagagcagcatcgacatcgagaacggcttcatcagcgagtcc cagtacacctatgccctgaaggagaaggccaagtatcagtgcaagctgggatacgtgaccgcagacggagagacatctggcagcatcacctgcggc aaggatggctggtctgcccagcccacatgcatcaagagcatcaagaccgactgtctgtctctgcccagctttgagaatgccatccctatgggcgag aagaaggacgtgtacaaggccggcgagcaggtgacatacacctgcgccacatactataagatggacggcgccagcaacgtgacctgtatcaattcc cggtggacaggcagacctacctgcagggatacaaagctgcgtgaacccacccaccgtgcagaatgcctatatcgtgtcccgccagatgtctaagtac cctagcggcgagcgggtgagatatcagtgccggtccccatacgagatgttcggcgacgaggaagtgatgtgcctgaacggcaattggacagagcct ccacagtgcaaggatagcaccggcaagtgtggaccacctccaccaatcgacaacggcgatatcacatcctttccactgagcgtgtacgcccccgcc tcctctgtggagtatcagtgccagaacctgtaccagctggagggcaataagcgcatcacctgtcggaacggccagtggtctgagcctccaaagtgc ctgcaccttgcgtgatctccagagagatcatggagaactataatatcgccctgcgctggacagccaagcagaagctgtactctcggaccggcgag agcgtggagttcgtgtgcaagcggggctatagactgagctcccgcagccacacactgcggaccacatgctgggacggcaagctggagtacccaacc tgtgccaagaggtgagcggccgctccataaagtaggaaacactacatccataaagtaggaaacactacatccataaagtaggaaacactacagcgg ccgcgtcgacacgcgtggtacctctagagtcgacccgggcggcctcgaggacggggtgaactacgcctgaggatccgatcttttttccctctgccaa aaattatggggacatcatgaagccccttgagcatctgacttctggctaataaaggaaatttattttcattgcaatagtgtgttggaattttttgtg
```

-continued tctctcactcggaagcaattcgttgatctgaatttcgaccacccataatacccattaccctggtagataagtagcatggcgggttaatcattaact acaaggaaccccctagtgatggagttggccactccctctctgcgcgctcgctcgctcactgaggccgggcgaccaaaggtcgcccgacgcccgggct ttgcccgggcggcctcagtgagcgagcgagcgcgcag >pAAVCBA-opt humanFH(NomiRT) rAAV vector nucleic acid sequence
                                                                    (SEQ ID NO: 6)
ctgcgcgctcgctcgctcactgaggccgcccgggcaaagcccgggcgtcgggcgacctttggtcgcccggcctcagtgagcgagcgagcgcgcaga gagggagtggccaactccatcactagggggttccttgtagttaatgattaacccgccatgctacttatctaccagggtaatggggatcctctagaac tatagctagtcgacattgattattgactagttattaatagtaatcaattacggggtcattagttcatagcccatatatggagttccgcgttacata acttacggtaaatggcccgcctggctgaccgcccaacgacccccgcccattgacgtcaataatgacgtatgttcccatagtaacgccaatagggac tttccattgacgtcaatgggtggagtatttacggtaaactgcccacttggcagtacatcaagtgtatcatatgccaagtacgccccctattgacgt caatgacggtaaatggcccgcctggcattatgcccagtacatgaccttatgggactttcctacttggcagtacatctacgtattagtcatcgctat taccatggtcgaggtgagccccacgttctgcttcactctccccatctcccccccctccccacccccaattttgtatttatttattttttaattatt ttgtgcagcgatggggcgggggggggggggggcgcgcgccaggcggggcggggcggggcgaggggcggggcggggcgaggcggagaggtgcggc ggcagccaatcagagcggcgcgctccgaaagtttccttttatggcgaggcggcggcggcggcggccctataaaaagcgaagcgcgcggcgggcggg gagtcgctgcgacgctgccttcgccccgtgccccgctccgccgccgcctcgcgccgcccgccccggctctgactgaccgcgttactcccacaggtg agcgggcgggacggcccttctcctccgggctgtaattagcgcttggtttaatgacggcttgtttcttttctgtggctgcgtgaaagccttgagggg ctccgggagggccctttgtgcgggggggagcggctcggggggtgcgtgcgtgtgtgtgtgcgtggggagcgccgcgtgcggctccgcgctgcccggc ggctgtgagcgctgcgggcgcggcgcggggctttgtgcgctccgcagtgtgcgcgaggggagcgcggccggggcggtgccccgcggtgcgggggg ggctgcgaggggaacaaaggctgcgtgcggggtgtgtgcgtggggggggtgagcagggggtgtgggcgcgtcggtcgggctgcaaccccccctgcac cccccctccccgagttgctgagcacggcccggcttcgggtgcggggctccgtacggggcgtggcgcgggggctcgccgtgccgggcgggggggtggcgg caggtggggggtgccgggcgggcggggcggggccgcctcgggccggggagggctcggggagggcgcggcggcccccgagcgccggcggctgtcgaggc gcggcgagccgcagccattgcctttttatggtaatcgtgcgagagggcgcagggacttcctttgtcccaaatctgtgcggagccgaaatctgggagg cgccgccgcacccctctagcgggcgcggggcgaagcggtgcggcgccggcaggaaggaaatgggcggggagggccttcgtgcgtcgccgcgccgc cgtccccttctccctctccagcctcggggctgtccgcggggggacggctgccttcggggggggacggggcagggcggggttcggcttctggcgtgtg accggcggctctagagcctctgctaaccatgttcatgccttcttcttttttcctacagctcctgggcaacgtgctggttattgtgctgtctcatcat tttggcaaagaattcgccaccatgcgcctgctggccaagatcatctgcctgatgctgtgggccatctgcgtggccgaggactgtaacgagctgccc cctcggagaaatacagagatcctgaccggctcttggagcgatcagacctacccagagggcacacaggccatctacaagtgcaggcccggctatcgc tccctgggcaatatcatcatggtgtgcaggaagggagagtgggtggccctgaacccactgagaaagtgccagaagaggccatgtggacacccaggc gacacacctttcggcacctttacactgaccggcggcaacgtgttcgagtacggcgtgaaggccgtgtatacctgcaatgagggctaccagctgctg ggcgagatcaactaccgggagtgtgacacagatggctggaccaatgatatccccatctgcgaggtggtgaagtgtctgccagtgaccgcccccgag aacggcaagatcgtgagctccgccatggagcctgacagagagtatcacttcggccaggccgtgaggttcgtgtgcaatagcggctacaagatcgag ggcgatgaggagatgcactgttccgacgatggcttctggtctaaggagaagcccaagtgcgtggagatctcctgtaagtctcctgacgtgattaac ggcagcccaatctcccagaagatcatctataaggagaatgagcggtttcagtacaagtgcaacatgggctacgagtattccgagagaggcgatgcc gtgtgcacagagtctggatggaggcccctgcctagctgcgaggagaagtccaccctgaagccttgtgactatccagatatcaagcacggcggcctg tatcacgagaatatgaggcgcccttacttcccagtggccgtgggcaagtactattcctactattgcgacgagcactttgagacaccatccggctct tactgggaccacatccactgtacccaggatggctggtctcccgccgtgccttgcctgagaaagtgttacttcccctatctggagaacggctacaac cagaattatggcaggaagtttgtgcagggcaagtccatcgacgtggcatgccacccaggatacgcactgcctaaggcacagaccacagtgacctgt atggagaatggctggagcccaacacccaggtgcatccgcgtgaagacctgttccaagagcagcatcgacatcgagaacggcttcatcagcgagtcc cagtacacctatgccctgaaggagaaggccaagtatcagtgcaagctgggatacgtgaccgcagacggagagacatctgcagcatcacctgcggc aaggatggctggtctgcccagcccacatgcatcaagagcatcaagaccgactgtctgtctctgcccagctttgagaatgccatccctatgggcgag aagaaggacgtgtacaaggccggcgagcaggtgacatacacctgcgccacatactataagatggacggcgccagcaacgtgacctgtatcaattcc -continued cggtggacaggcagacctacctgcagggatacaagctgcgtgaacccacccaccgtgcagaatgcctatatcgtgtcccgccagatgtctaagtac cctagcggcgagcgggtgagatatcagtgccggtccccatacgagatgttcggcgacgaggaagtgatgtgcctgaacggcaattggacagagcct ccacagtgcaaggatagcaccggcaagtgtggaccacctccaccaatcgacaacggcgatatcacatcctttccactgagcgtgtacgcccccgcc tcctctgtggagtatcagtgccagaacctgtaccagctggagggcaataagcgcatcacctgtcggaacggccagtggtctgagcctccaaagtgc ctgcaccttgcgtgatctccagagagatcatggagaactataatatcgccctgcgctggacagccaagcagaagctgtactctcggaccggcgag agcgtggagttcgtgtgcaagcggggctatagactgagctcccgcagccacacactgcggaccacatgctgggacgggcaagctggagtacccaacc tgtgccaagaggtgagcggccgcgtcgacacgcgtggtacctctagagtcgacccgggcggcctcgaggacggggtgaactacgcctgaggatccg atctttttccctctgccaaaaattatggggacatcatgaagccccttgagcatctgacttctggctaataaaggaaatttattttcattgcaatag tgtgttggaattttttgtgtctctcactcggaagcaattcgttgatctgaatttcgaccaccataatacccattaccctggtagataagtagcat ggcgggttaatcattaactacaaggaacccctagtgatggagttggccactccctctctgcgcgctcgctcgctcactgaggccgggcgaccaaag gtcgcccgacgcccgggctttgcccgggcggcctcagtgagcgagcgagcgcgcag >pAAVss-CB-Opt-humanFH rAAV vector nucleic acid sequence (SEQ ID NO: 7)
ttggccactccctctctgcgcgctcgctcgctcactgaggccgggcgaccaaaggtcgcccgacgcccgggctttgcccgggcggcctcagtgagc gagcgagcgcgcagagagggagtggccaactccatcactaggggttcctacgcgtcgacattgattattgactctggtcgttacataacttacggt aaatggcccgcctggctgaccgcccaacgaccccgcccattgacgtcaataatgacgtatgttcccatagtaacgccaataggggactttccattga cgtcaatgggtggagtatttacggtaaactgcccacttggcagtacatcaagtgtatcatatgccaagtacgccccctattgacgtcaatgacggt aaatggcccgcctggcattatgcccagtacatgaccttatgggactttcctacttggcagtacatctactcgaggccacgttctgcttcactctcc ccatctcccccccctccccacccccaattttgtatttatttattttttaattattttgtgcagcgatgggggcggggggggggggggggggcgc gcgccaggcggggcggggcggggcgaggggcggggcggggcgaggcggagaggtgcggcggcagccaatcagagcggcgcgctccgaaagtttcct tttatggcgaggcggcggcggcggcggccctataaaaagcgaagcgcgcggcgggcgggagcgggatcagccaccgcggtggcggccctagagtcg atcgaggaactgaaaaaccagaaagttaactggtaagtttagtctttttgtcttttatttcaggtcccgatccggtggtggtgcaaatcaaagaa ctgctcctcagtggatgttgcctttacttctaggcctgtacggaagtgttacttctgctctaaaagctgcggaattgtacccgcggccgatccacc ggtatcgatgccaccatgagacttctagcaaagattatttgccttatgttatgggctatagtgtagcagaagattgcaatgaacttcctccaagaa gaaatacagaaattctgacaggacctggtctgaccaaacatatccagaaggcacccaggctatctataaatgccgccctggatatagatctcttgg aaatataataatggtatgcaggaagggagaatgggttgctcttaatccattaaggaaatgtcagaaaaggccctgtggacatcctggagatactcc ttttggtacttttaccccttacaggaggaaatgtgtttgaatatggtgtaaaagctgtgtatacatgtaatgaggggtatcaattgctaggtgagat taattaccgtgaatgtgacacagatggatggaccaatgatattcctatatgtgaagttgtgaagtgtttaccagtgacagcaccagagaatggaaa aattgtcagtagtgcaatggaaccagatcgggaataccatttttggacaagcagtacggtttgtatgtaactcaggctacaagattgaaggagatga agaaatgcattgttcagacgatggtttttggagtaaaagagaaaccaaagtgtgtggaaatttcatgcaaatccccagatgttatataatggatctcc tatatctcagaagattatttataaggagatgaacgatttcaatataaatgtaacatgggttatgaatacagtgaaagaggagatgctgtatgcac tgaatctggatggcgtccgttgccttcatgtgaagaaaaatcaaccttgaaaccttgtgattatccagacattaaacatggaggtctatatcatga gaatatgcgtagaccatactttccagtagctgtaggaaaatattactcctattactgtgatgaacattttgagactccgtcaggaagttactggga tcacattcattgcacacaagatggatggtcgccagcagtaccatgcctcagaaatgttatttttccttatttggaaaatggatataatcaaaatta tggaagaaagtttgtacagggtaaatctatagacgttgcctgccatcctggctacgctcttccaaaagcgcagaccacagttacatgtatggagaa tggctggtctcctactcccagatgcatccgtgtcaaaacatgttccaaatcaagtatagatattgagaatgggtttatttctgaatctcagtatac atatgcccttaaaagaaaaagcaaaatatcaatgcaaactaggatatgtaacagcagatggtgaaacatcaggatcaattacatgtgggaaagatgg atggtcagctcaacccacgtgcattaaatctataaaaacagattgtctcagtttacctagctttgaaaatgccatacccatgggagagaagaagga tgtgtataaggcggggtgagcaagtgacttacacttgtgcaacatattacaaaatggatggagccagtaatgtaacatgcattaatagcagatggac aggaaggccaacatgcagagacacctcctgtgtgaatccgcccacagtacaaaatgcttatatagtgtcgagacagatgagtaaatatccatctgg tgagagagtacgttatcaatgtaggagcccttatgaaatgtttgggggatgaagaagtgatgtgtttaaatggaaactggacggaaccacctcaatg caaagattctacaggaaaatgtgtgggcccctccacctattgacaatgggggacattacttcattcccgttgtcagtatatgctccagcttcatcagt -continued tgagtaccaatgccagaacttgtatcaacttgagggtaacaagcgaataacatgtagaaatggacaatggtcagaaccaccaaaatgcttacatcc gtgtgtaatatcccgagaaattatggaaaattataacatagcattaaggtggacagccaaacagaagctttattcgagaacaggtgaatcagttga atttgtgtgtaaacggggatatcgtctttcatcacgttctcacacattgcgaacaacatgttgggatgggaaactggagtatccaacttgtgcaaa aagataggcggccgctccataaagtaggaaacactacatccataaagtaggaaacactacatccataaagtaggaaacactacagccggccgcgtcg actgatcagcctcgactgtgccttctagttgccagccatctgttgtttgcccctcccccgtgccttccttgaccctggaaggtgccactccactg tcctttcctaataaaatgaggaaattgcatcgcattgtctgagtaggtgtcattctattctggggggtggggtggggcaggacagcaagggggagg attgggaagacaagatctaggaacccctagtgatggagttggccactccctctctgcgcgctcgctcgctcactgaggccgcccgggcaaagcccg ggcgtcgggcgacctttggtcgcccggcctcagtgagcgagcgagcgcgcagagagggagtggccaa >pAAVss-CB-Opt-humanFH No miR142T rAAV vector nucleic acid sequence (SEQ ID NO: 8)

ttggccactccctctctgcgcgctcgctcgctcactgaggccgggcgaccaaaggtcgcccgacgcccgggctttgcccgggcggcctcagtgagc gagcgagcgcgcagagagggagtggccaactccatcactaggggttcctacgcgtcgacattgattattgactctggtcgttacataacttacggt aaatggcccgcctggctgaccgcccaacgacccgcccattgacgtcaataatgacgtatgttcccatagtaacgccaatagggactttccattga cgtcaatgggtggagtatttacggtaaactgcccacttggcagtacatcaagtgtatcatatgccaagtacgcccctattgacgtcaatgacggt aaatggcccgcctggcattatgcccagtacatgaccttatgggactttcctacttggcagtacatctactcgaggccacgttctgcttcactctcc ccatctcccccccctccccacccccaattttgtatttatttattttttaattattttgtgcagcgatggggcggggggggggggggggggggggcgc gcgccaggcggggcggggcggggcgaggggcggggcggggcgaggcggagaggtgcggcggcagccaatcagagcggcgcgctccgaaagtttcct tttatggcgaggcggcggcggcggcggccctataaaaagcgaagcgcgcggcgggcgggagcgggatcagccaccgcggtggcggccctagagtcg atcgaggaactgaaaaaccagaaagttaactggtaagtttagtcttttgtctttatttcaggtcccggatccggtggtggtgcaaatcaaagaa ctgctcctcagtggatgttgcctttacttctaggcctgtacggaagtgttacttctgctctaaaagctgcggaattgtacccgcggccgatccacc ggtatcgatgccaccatgagacttctagcaaagattatttgccttatgttatgggctatagtgtagcagaagattgcaatgaacttcctccaagaa gaaatacagaaattctgacaggacctggtctgaccaaacatatccagaaggcacccaggctatctataaatgccgccctggatatagatctcttgg aaatataataatggtatgcaggaagggagaatgggttgctcttaatccattaaggaaatgtcagaaaaggccctgtggacatcctggagatactcc ttttggtacttttaccttacaggaggaaatgtgtttgaatatggtgtaaaagctgtgtatacatgtaatgaggggtatcaattgctaggtgagat taattaccgtgaatgtgacacagatggatggaccaatgatattcctatatgtgaagttgtgaagtgtttaccagtgacagcaccagagaatggaaa aattgtcagtagtgcaatggaaccagatcgggaataccatttttggacaagcagtacggtttgtatgtaactcaggctacaagattgaaggagatga agaaatgcattgttcagacgatggttttttggagtaaagagaaaccaaagtgtgtggaaatttcatgcaaatccccagatgttataaatggatctcc tatatctcagaagattatttataaggagaatgaacgattttcaatatatatgtaacatgggttatgaatacagtgaaagaggagatgctgtatgcac tgaatctggatggcgtccgttgcccttcatgtgaagaaaaatcaaccttgaaaccttgtgattatccagacattaaacatggaggtctatatcatga gaatatgcgtagaccatactttccagtagctgtaggaaaatattactcctattactgtgatgaacattttgagactccgtcaggaagttactggga tcacattcattgcacacaagatggatggtcgccagcagtaccatgcctcagaaaatgttattttccttatttggaaaatggatataatcaaaatta tggaagaaagtttgtacagggtaaatctatagacgttgcctgccatcctggctacgctcttccaaaagcgcagaccacagttacatgtatgtggagaa tggctggtctcctactcccagatgcatccgtgtcaaaacatgttccaaatcaagtatagatattgagaatgggtttattttctgaatctcagtatac atatgccttaaaagaaaaagcaaaatatcaatgcaaactaggatatgtaacagcagatggtgaaacatcaggatcaattacatgtgggaaagatgg atggtcagctcaacccacgtgcattaaatctataaaaacagattgtctcagtttacctagctttgaaaatgccatacccatgggagagaagaagga tgtgtataaggcgggtgagcaagtgacttacacttgtgcaacatattacaaaatggatggagccagtaatgtaacatgcattaatagcagatggac aggaaggccaacatgcagagacacctcctgtgtgaatccgcccacagtacaaaatgcttatatagtgtcgagacagatgagtaaatatccatctgg tgagagtacgttatcaatgtaggagcccttatgaaatgtttggggatgaagaagtgatgtgtttaaatggaaactggacggaaccacctcaatg caaagattctacaggaaaatgtgggcccctccacctattgacaatggggacattacttcattcccgttgtcagtatatgctccagcttcatcagt tgagtaccaatgccagaacttgtatcaacttgagggtaacaagcgaataacatgtagaaatggacaatggtcagaaccaccaaaatgcttacatcc gtgtgtaatatcccgagaaattatggaaaattataacatagcattaaggtggacagccaaacagaagctttattcgagaacaggtgaatcagttga -continued atttgtgtgtaaacggggatatcgtctttcatcacgttctcacacattgcgaacaacatgttgggatgggaaactggagtatccaacttgtgcaaa aagataggcggccgcgtcgactgatcagcctcgactgtgccttctagttgccagccatctgttgtttgcccctcccccgtgccttccttgaccctg gaaggtgccactcccactgtcctttcctaataaaatgaggaaattgcatcgcattgtctgagtaggtgtcattctattctggggggtggggtgggg caggacagcaaggggggaggattgggaagacaagatctaggaacccctagtgatggagttggccactccctctctgcgcgctcgctcgctcactgag gccgccgggcaaagcccgggcgtcgggcgacctttggtcgcccggcctcagtgagcgagcgagcgcgcagagagggagtggccaa >Short CMV enhancer nucleic acid sequence (SEQ ID NO: 9)

tacggtaaatggcccgcctggctgaccgcccaacgacccegcccattgacgtcaataatgacgtatgttcccatagtaacgccaatagggactttc cattgacgtcaatgggtggagtatttacggtaaactgcccacttggcagtacatcaagtgtatcatatgccaagtacgccccctattgacgtcaat gacggtaaatggcccgcctggcattatgcccagtacatgaccttatgggactttcctacttggcagtacatctactcgaggccacgttctgctt >Long CMV enhancer nucleic acid sequence (SEQ ID NO: 10)

tcaatattggccattagccatattattcattggttatatagcataaatcaatattggctattggccattgcatacgttgtatctatatcataatat gtacatttatattggctcatgtccaatatgaccgccatgttggcattgattattgactagttattaatagtaatcaattacggggtcattagttca tagcccatatatggagttccgcgttacataacttacggtaaatggcccgcctggctgaccgcccaacgacccccgcccattgacgtcaataatgac gtatgttcccatagtaacgccaatagggactttccattgacgtcaatgggtggagtatttacggtaaactgcccacttggcagtacatcaagtgta tcatatgccaagtccgccccctattgacgtcaatgacggtaaatggcccgcctggcattatgcccagtacatgaccttacgggactttcctacttg gcagtacatctac >Short CB Promoter nucleic acid sequence (SEQ ID NO: 11)

tctccccatctcccccccctccccacccccaattttgtatttatttatttttttaattattttgtgcagcgatggggcggggggggggggggggggg ggcgcgcgccaggcggggcggggcggggcgaggggcggggcggggcgaggcggagaggtgcggcggcagccaatcagagcggcgcgctccgaaagt ttcctttttatggcgaggcggcggcggcggcggcggccctataaaaagcgaagcgcgcggcgggcgggagcgggatc >Long CB Promoter nucleic acid sequence (SEQ ID NO: 12)

acgtattagtcatcgctattaccatggtcgaggtgagccccacgttctgcttcactctccccatctcccccccctccccacccccaattttgtatt tatttattttttaattattttgtgcagcgatggggcggggggggggggggggggcgcgcgccaggcggggcggggcggggcgaggggcggggcgggg cgaggcggagaggtgcggcggcagccaatcagagcggcgcgctccgaaagtttcctttttatggcgaggcggcggcggcggcggcggccctataaaaagc gaagcgcgcggcgggcgg >Artificial intron 1 nucleic acid sequence (SEQ ID NO: 13)

gaactgaaaaaccagaaagttaactggtaagtttagtcttttttgtcttttatttcaggtcccggatccggtggtggtgcaaatcaaagaactgctc ctcagtggatgttgcctttacttctaggcctgtacggaagtgttacttctgctctaaaagctgcggaattgtaccc >Artificial intron 2 nucleic acid sequence (SEQ ID NO: 14)

gagtcgctgcgcgctgccttcgccccgtgccccgctccgccgccgcctcgcgccgcccgccccggctctgactgaccgcgttactcccacaggtga gcgggcgggacggcccttctcctccgggctgtaattagcgcttggtttaatgacggcttgtttcttttctgtggctgcgtgaaagccttgaggggc tccgggagggccctttgtgcggggggggagcggctcggggggtgcgtgcgtgtgtgtgcgtggggagcgccgcgtgcggctccgcgctgcccggc ggctgtgagcgctgcgggcgcggcgcggggctttgtgcgctccgcagtgtgcgcgaggggagcgcggccggggcggtgccccgcgtgcgggggg ggctgcgaggggaacaaaggctgcgtgcggggtgtgtgcgtggggggggtgagcagggggtgtgggcgcgtcggtcgggctgcaacccccccctgcac cccctccccgagttgctgagcacggcccggcttcgggtgcggggctccgtacggggcgtggcgcggggctcgccgtgccgggcggggggtggcgg caggtggggggtgccgggcggggcggggccgcctcgggccgggagggctcggggagggcgcggcggccccegagcgccggcggctgtcgaggc gcggcgagccgcagccattgcctttatggtaatcgtgcgagagggcgcagggacttcctttgtcccaaatctgtgcggagccgaaatctgggagg cgccgccgcacccctctagcgggcgcggggcgaagcggtgcggcgccggcaggaaggaaatgggcgggagggccttcgtgcgtcgccgcgccgc cgtccccttctccctctccagcctcggggctgtccgcggggggacggctgccttcgggggggacggggcagggcgggttcggcttctggcgtgtg accggcggctctagagcctctgctaaccatgttcatgccttcttcttttttcctacagctcctgggcaacgtgctggttattgtgctgtctcatcat tttggcaaag -continued >Artificial intron 3 (chicken beta-actin intron) nucleic acid sequence (SEQ ID NO: 15)

gtgagcgggcgggacggcccttctcctccgggctgtaattagcgcttggtttaatgacggcttgtttcttttctgtggctgcgtgaaagccttgag gggctccgggagggcccttgtgcggggggagcggctcggggggtgcgtgcgtgtgtgtgtgcgtggggagcgccgcgtgcggctccgcgctgccc ggcggctgtgagcgctgcgggcgcggcgcggggctttgtgcgctccgcagtgtgcgcgaggggagcgcggccgggggcggtgccccgcggtgcggg gggggctgcgaggggaacaaaggctgcgtgcggggtgtgtgcgtggggggtgagcaggggggtgtgggcgcgtcggtcgggctgcaacccccctg cacccccctccccgagttgctgagcacggcccggcttcgggtgcggggctccgtacggggcgtggcgcggggctcgccgtgccgggcggggggtgg cggcaggtggggggtgccgggcggggcggggccgcctcgggccggggagggctcggggagggggcgcggcggcccccggagcgccggcggctgtcga ggcgcggcgagccgcagccattgccttttatggtaatcgtgcgagagggcgcagggacttcctttgtcccaaatctgtgcggagccgaaatctggg aggcgccgccgcaccccctctagcgggcgcggggcgaagcggtgcggcgccggcaggaaggaaatgggcggggagggccttcgtgcgtcgccgcgc cgccgtcccccttctccctctccagcctcggggctgtccgcgggggggacggctgccttcggggggggacggggcagggcggggttcggcttctggcgt gtgaccggcggctctagagcctctgctaaccatgttcatgccttcttcttttttcctacagctcctgggcaacgtgctggttattgtgctgtctcat cattttggcaaag >3X miR-142t binding site (SEQ ID NO: 16)

ggccgctccataaagtaggaaacactacatccataaagtaggaaacactacatccataaagtaggaaacactacagc

>BGH 3'UTR-polyA-GRE partial nucleic acid sequence (SEQ ID NO: 17)

ctcgactgtgccttctagttgccagccatctgttgtttgcccctcccccgtgccttccttgaccctggaaggtgccactcccactgtcctttccta ataaaatgaggaaattgcatcgcattgtctgagtaggtgtcattctattctggggggtggggtggggcaggacagcaaggggggaggattgggaaga caa >Rabbit globulin poly A nucleic acid sequence (SEQ ID NO: 18)

gatctttttccctctgccaaaaattatggggacatcatgaagccccttgagcatctgacttctggctaataaaggaaatttattttcattgcaata gtgtgttggaatttttttgtgtctctcactcg >Kozak sequence (SEQ ID NO: 19)

gccacc

>rAAV CBA-FH (SEQ ID NO: 20)

ctgcgcgctcgctcgctcactgaggccgcccgggcaaagcccgggcgtcgggcgacctttggtcgcccggcctcagtgagcgagcgagcgcgcaga gagggagtggccaactccatcactaggggttccttgtagttaatgattaagacattgattattgactagttattaatagtaatcaattacggggtc attagttcatagcccatatatggagttccgcgttacataacttacggtaaatggcccgcctggctgaccgcccaacgacccccgcccattgacgtc aataatgacgtatgttcccatagtaacgccaataggacttttccattgacgtcaatgggtggactatttacggtaaactgcccacttggcagtaca tcaagtgtatcatatgccaagtacgccccctattgacgtcaatgacggtaaatggcccgcctggcattatgcccagtacatgaccttatgggactt tcctacttggcagtacatctacgtattagtcatcgctattaccatgggtcgaggtgagccccacgttctgcttcactctccccatctcccccccct ccccacccccaattttgtatttatttattttttaattattttgtgcagcgatgggggcggggggggggggggcgcgcgccaggcggggcggggcgg ggcgaggggcggggcggggcgaggcggagaggtgcggcggcagccaatcagagcggcgcgctccgaaagtttccttttatggcgaggcggcggcgg cggcggccctataaaaagcgaagcgcgcggcgggcgggagtcgctgcgttgccttcgccccgtgccccgctccgcgccgcctcgcgccgcccgccc cggctctgactgaccgcgttactcccacaggtgagcgggcgggacggcccttctcctccgggctgtaattagcgcttggtttaatgacggctcgtt tcttttctgtggctgcgtgaaagccttaaagggctccgggagggccctttgtgcggggggagcggctcggggggtgcgtgcgtgtgtgtgtgcgt ggggagcgccgcgtgcggcccgcgctgcccggcggctgtgagcgctgcgggcgcggcgcggggctttgtgcgctccgcgtgtgcgcgaggggagcg cggccggggcggtgccccgcggtgcggggggctgcgaggggaacaaaggctgcgtgcggggtgtgtgcgtggggggtgagcagggggtgtggg cgcggcggtcgggctgtaaccccccctgcacccccctccccgagttgctgagcacggcccggcttcgggtgcggggctccgtgcggggcgtggcg cggggctcgccgtgccgggcggggggtggcggcaggtggggggtgccgggcggggcggggcggggccgcctcgggccggggagggctcggggagggggcgcg gcggccccggagcgccggcggctgtcgaggcgcggcgagccgcagccattgccttttatggtaatcgtgcgagagggcgcagggacttcctttgtc -continued

```
ccaaatctggcggagccgaaatctgggaggcgccgccgcaccccctctagcgggcgcgggcgaagcggtgcggcgccggcaggaaggaaatgggcg gggagggccttcgtgcgtcgccgcgccgccgtccccttctccatctccagcctcggggctgccgcaggggacggctgccttcggggggacgggg cagggcggggttcggcttctggcgtgtgaccggcggctctagagcctctgctaaccatgttcatgccttcttcttttcctacagctcctgggcaa cgtgctggttgttgtgctgtctcatcattttggcaaagaattggacgttgtgaacagagttagctggtaaatgtcctcttaaaagatccaaaaaat gagacttctagcaaagattatttgccttatgttatgggctatttgtgtagcagaagattgcaatgaacttcctccaagaagaaatacagaaattct gacaggttcctggtctgaccaaacatatccagaaggcacccaggctatctataaatgccgccctggatatagatctcttggaaatataataatggt atgcaggaagggagaatgggttgctcttaatccattaaggaaatgtcagaaaaggccctgtggacatcctggagatactccttttggtactttac ccttacaggaggaaatgtgtttgaatatggtgtaaaagctgtgtatacatgtaatgaggggtatcaattgctaggtgagattaattaccgtgaatg tgacacagatggatggaccaatgatattcctatatgtgaagttgtgaagtgtttaccagtgacagcaccagagaatggaaaaattgtcagtagtgc aatggaaccagatcgggaataccattttggacaagcagtacggtttgtatgtaactcaggctacaagattgaaggagatgaagaaatgcattgttc agacgatggttttggagtaaagagaaaccaaagtgtgtggaaatttcatgcaaatccccagatgttatataatggatctcctatatctcagaagat tatttataaggagaatgaacgatttcaatatataatgtaacatgggttatgaatacagtgaaagaggagatgctgtatgcactgaatctggatggcg tccgagcatcatgtgaagaaaaatcaaccttgaaaccagtgattatccagacattaaacatggaggtctatatcatgagaatatgcgtagaccata ctttccagtagctgtaggaaaatattactcctattactgtgatgaacattttgagactccgtcaggaagttactgggatcacattcattgcacaca agatggatggtcgccagcagtaccatgcctcagaaaatgttattttccttatttggaaaatggatataatcaaaattatggaagaaagtttgtaca gggtaaatctatagacgttgcctgccatcctggctacgctcttccaaaagcgcagaccacagttacatgtatggagaatggctggtctcctactcc cagatgcatccgtgtcaaaacatgttccaaatcaagtatagatattgagaatgggtttatttctgaatctcagtatacatatgccttaaaagaaaa agcaaaatatcaatgcaaactaggatatgtaacagcagatggtgaaacatcaggatcaattacatgtgggaaagatggatggtcagctcaacccac gtgcattaaatctataaaaacagattgtctcagtttacctagctttgaaaatgccatacccatgggagagaagaaggatgtgtataaggcgggtga gcaagtgacttacacttgtgcaacatattacaaaatggatggagccagtaatgtaacatgcattaatagcagatggacaggaaggccaacatgcag agacacctcctgtgtgaatccgcccacagtacaaaatgcttatatagtgtcgagacagatgagtaaatatccatctggtgagagagtacgttatca atgtaggagcccttatgaaatgtttggggatgaagaagtgatgtgtttaaatggaaactggacggaaccacctcaatgcaaagattctacaggaaa atgtgggcccctccacctattgacaatggggacattacttcattcccgttgtcagtatatgctccagcttcatcagttgagtaccaatgccagaa cttgtatcaacttgagggtaacaagcgaataacatgtagaaatggacaatggtcagaaccaccaaaatgcttacatccgtgtgtaatatcccgaga aattatggaaaattataacatagcattaaggtggacagcccaaacagaagctttattcgagaacaggtgaatcagttgaatttgtgtgtaaacgggg atatcgtctttcatcacgttctcacacattgcgaacaacatgttgggatgggaaactggagtatccaacttgtgcaaaaagatagaattcactcct caggtgcaggctgcctatcagaaggtggtggctggtgtggccaatgccctggctcacaaataccactgagatctttttccctctgccaaaaattat ggggacatcatgaagcccttgagcatctgacttctggctaataaaggaaatttattttcattgcaatagtgtgttggaattttttgtgtctctca ctcggaaggtggcgggttaatcattaactacaaggaacccctagtgatggagttggccactccctctctgcgcgctcgctcgctcactgaggccgg gcgaccaaaggtcgcccgacgcccgggctttgcccgggcggcctcagtgagcgagcgagcgcgcag
```

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

---

What is claimed is:

1. An isolated nucleic acid encoding the amino acid sequence set forth in SEQ ID NO: 3, wherein the nucleic acid sequence is operably linked to SEQ ID NO: 19 and SEQ ID NO: 14, and further comprises a promoter comprising the nucleic acid sequence set forth in SEQ ID NOs: 10 and 12.

2. The isolated nucleic acid of claim 1, wherein the nucleic acid comprises the sequence set forth in SEQ ID NO: 4.

3. The isolated nucleic acid of claim 1, wherein the promoter further comprises an enhancer sequence, wherein the enhancer sequence comprises the sequence set forth in SEQ ID NO: 9 or 10.

4. The isolated nucleic acid of claim 1, wherein the isolated nucleic acid comprises one or more introns.

5. The isolated nucleic acid of claim 4, wherein at least one intron is positioned between the promoter and the nucleic acid sequence.

6. The isolated nucleic acid of claim 4, wherein at least one intron comprises the sequence set forth in any one of SEQ ID NOs: 13-15.

7. The isolated nucleic acid of claim 1 further comprising a 3' untranslated region (3'UTR).

8. The isolated nucleic acid of claim 7, wherein the 3'UTR comprises the sequence set forth in SEQ ID NO: 17 or 18.

9. A vector comprising the isolated nucleic acid of claim 1.

10. The vector of claim 9, wherein the vector is a plasmid or a viral vector.

11. The vector of claim 10, wherein the viral vector is an adenoviral vector, adeno-associated virus vector, a lentiviral vector, a retroviral vector, or a Baculovirus vector.

12. A host cell comprising the vector of claim 9.

13. The host cell of claim 12, wherein the host cell is a mammalian cell, yeast cell, bacterial cell, or insect cell.

14. A recombinant adeno-associated virus (rAAV) comprising:

(i) the isolated nucleic acid of claim 1; and (ii) an adeno-associated virus (AAV) capsid protein.

15. The rAAV of claim 14, wherein the capsid protein has a tropism for muscle tissue or ocular tissue.

16. The rAAV of claim 14, wherein the capsid protein is of a serotype selected from AAV1, AAV2, AAV3, AAV4, AAV5, AAV6, AAV7, AAV8, AAV9, or a variant thereof.

\* \* \* \* \*